US012145120B2

(12) United States Patent
Mitra et al.

(10) Patent No.: US 12,145,120 B2
(45) Date of Patent: Nov. 19, 2024

(54) LIQUID ENCAPSULATION METHOD AND COMPOSITIONS AND USES RELATED THERETO

(71) Applicants: Sushanta Mitra, Waterloo (CA); Sirshendu Misra, Waterloo (CA)

(72) Inventors: Sushanta Mitra, Waterloo (CA); Naga Siva Kumar Gunda, Waterloo (CA); Sirshendu Misra, Waterloo (CA); Kumari Trinavee, Mississauga (CA)

(*) Notice: Subject to any disclaimer, the term of this patent is extended or adjusted under 35 U.S.C. 154(b) by 0 days.

(21) Appl. No.: 17/432,848

(22) PCT Filed: Feb. 20, 2020

(86) PCT No.: PCT/CA2020/050222
§ 371 (c)(1),
(2) Date: Aug. 20, 2021

(87) PCT Pub. No.: WO2020/168432
PCT Pub. Date: Aug. 27, 2020

(65) Prior Publication Data
US 2022/0055007 A1    Feb. 24, 2022

Related U.S. Application Data

(60) Provisional application No. 62/906,540, filed on Sep. 26, 2019.

(30) Foreign Application Priority Data

Feb. 21, 2019   (IN) .............................. 201911006813

(51) Int. Cl.
B01J 13/16    (2006.01)
B01J 13/08    (2006.01)
(Continued)

(52) U.S. Cl.
CPC ............... *B01J 13/16* (2013.01); *B01J 13/08* (2013.01); *B01J 13/206* (2013.01); *B01J 13/22* (2013.01)

(58) Field of Classification Search
None
See application file for complete search history.

(56) References Cited

U.S. PATENT DOCUMENTS 6,841,593 B2    1/2005  Kommareddi et al.
2003/0230818 A1  12/2003 Naveen et al.
(Continued)

FOREIGN PATENT DOCUMENTS

GB    762700 A      12/1956
WO    WO-95/28227 A1   10/1995
WO    WO-2016/142637 A1  9/2016

OTHER PUBLICATIONS

Extended European Search Report for EP Application No. 20759554.7 dated Sep. 16, 2022.
(Continued)

*Primary Examiner* — Jeffrey D Washville
(74) *Attorney, Agent, or Firm* — Foley Hoag LLP; David P. Halstead

(57) ABSTRACT

Present disclosure provides a method of forming a liquid-encapsulated core material, encapsulated core material compositions, and uses thereof, where the encapsulated core material is formed by providing an interfacial fluid layered on a host fluid, and passing a core material through the interfacial fluid and into the host fluid such that the interfacial fluid forms a shell around the core material. By so encapsulating the core material, it is protected from the host fluid.

30 Claims, 10 Drawing Sheets

(51) Int. Cl.
B01J 13/20 (2006.01)
B01J 13/22 (2006.01)

(56) References Cited

U.S. PATENT DOCUMENTS

2018/0146704 A1  5/2018  Ramon Real et al.
2019/0031987 A1  1/2019  Hollenkamp
2020/0114326 A1*  4/2020  Oxley .................. B01J 13/16

OTHER PUBLICATIONS

Abkarian et al., "Gravity-Induced Encapsulation of Liquids by Destabilization of Granular Rafts," Nature Communications, 2013, vol. 4: 1895.
Berry et al., "Measurement of Surface and Interfacial Tension Using Pendant Drop Tensiometry," Journal of Colloid and Interface Science, 2015, vol. 454, pp. 226-237.
International Patent Application No. PCT/CA2020/050222, International Preliminary Report on Patentability dated Aug. 10, 2021.
International Search Report for International Application No. PCT/CA2020/050222 dated Apr. 20, 2020.
Jambon-Puillet et al., "Drops Floating on Granular Rafts: A Tool for Liquid Transport and Delivery," Langmuir, 2018, vol. 34, pp. 4437-4444.
Kumar et al., "Wrapping With a Splash: High-Speed Encapsulation With Ultrathin Sheets," Science, 2018, vol. 359, pp. 775-778.
Loscertales et al., "Micro/Nano Encapsulation via Electrified Coaxial Liquid Jets," Science, Mar. 2002, vol. 295, pp. 1695-1698.
Misra et al., "Encapsulation with an Interfacial Liquid Layer: Robust and Efficient Liquid-Liquid Wrapping". Journal of Colloid and Interface Science, Sep. 27, 2019 (Sep. 27, 2019), vol. 558, pp. 334-344, https://www.sciencedirect.com/science/article/pii/S0021979719311427.
Trinavee et al., "Anomalous Wetting of Underliquid Systems: Oil Drops in Water and Water Drops in Oil," Langmuir, 2018, vol. 34, pp. 11695-11705.
Utada et al., "Monodisperse Double Emulsions Generated From a Microcapillary Device," Science, Apr. 2005, vol. 308, pp. 537-541.
Yin et al., "Triple-layered Encapsulation Through Direct Droplet Impact," Journal of Colloid and Interface Science, Jun. 2022, vol. 615, pp. 887-896.
Waghmare et al.," Drop Deposition on Under-liquid Low Energy Surfaces", Soft Matter, 2013, vol. 9, pp. 7437-7447.
Wang et al., "Do We Understand the Bubble Formation by a Single Drop Impacting Upon Liquid Surface?," Physics of Fluids, 2013, vol. 25, pp. 101702.
Worthington et al., "Impact with a Liquid Surface, Studied by the Aid of Instantaneous Photography," Proceedings of the Royal Society, 1877, vol. 25, pp. 137-148.
Worthington et al., "On Impact with a Liquid Surface," Proceedings of the Royal Society, February 1882, vol. 25, pp. 217-230.
Xiao et al., "A Novel Method for Preparing Epoxy-containing Microcapsules via Uv Irradiation-induced Interfacial Copolymerization in Emulsions," Polymer, 2007, vol. 48, pp. 4765-4776.
Yang et al., "Motions of a Fluid Drop Near a Deformable Interface, "International Journal of Multiphase Flow, 1990, vol. 16 (4), pp. 597-616.
Anna et al., "Formation of Dispersions Using Flow Focusing in Microchannels", Applied Physics Letters, 2003, vol. 82 (3), pp. 364-366.
Antkowiak et al., "Instant Fabrication and Selection of Folded Structures Using Drop Impact," Proceedings of the National Academy of Sciences of the United States of America, Jun. 2011, vol. 108(26), pp. 10400-10404.
Aristoff et al., "Water Entry of Small Hydrophobic Spheres," Journal of Fluid Mechanics, Jan. 2009, vol. 619, pp. 45-78.
Aussillous et al., "Properties of Liquid Marbles," Proceedings of the Royal Society A, Jan. 2006, vol. 462, pp. 973-999.

Aussillous et al., "Liquid marbles", Nature, 2001, vol. 411(6840), pp .924-927.
Berger et al., "Flavours and Fragrances Chemistry, Bioprocessing and Sustainability," Springer, pp. 1-649.
Bergmann et al., "Controlled Impact of a Disk on a Water Surface: Cavity Dynamics.," Journal of Fluid Mechanics, Oct. 2009, vol. 633, pp. 1-34.
Binks et al., "Solid Wettability From Surface Energy Components: Relevance to Pickering Emulsions," Langmuir, 2002, vol. 18, pp. 1270-1273.
Bonn et al., "Wetting and Spreading," Reviews of Modern Physics, April-Jun. 2009, vol. 81(2), pp. 739-805.
Casanova et al., "Encapsulation of Cosmetic Active Ingredients for Topical Application - A Review," Journal of Microencapsulation, 2016, vol. 33(1), pp. 1-56.
Chu et al., "Monodisperse Thermoresponsive Microgels with Tunable vol. Phase Transition Kinetics," Advanced Functional Materials, Nov. 2007, vol. 17, pp. 3499-3504.
Cole et al., "Challenges and Opportunities in the Encapsulation of Liquid and Semi-solid Formulations Into Capsules for Oral Administration", Advanced Drug Delivery Reviews, 2008, vol. 60(6), pp. 747-756.
Cox et al., The Dynamics of the Spreading of Liquids on a Solid Surface. Part 1. Viscousow, Journal of Fluid Mechanics, 1986 Vol. 168 pp. 169-194.
Cui et al.,"Stabilizing Liquid Drops in Nonequilibrium Shapes by the Interfacial Jamming of Nanoparticles", Science, vol. 342, pp. 460-463. (2013).
Davidovitcha et al., "Prototypical Model for Tensional Wrinkling in Thin Sheets," Proceedings of the National Academy of Sciences of the United States of America, Nov. 2011, vol. 108(45), p. 18227-18232.
Fang et al., "Encapsulation of Polyphenols-a Review," Trends in Food Science Technology, 2010, vol. 21, pp. 510-523.
Gennes et al., "Capillarity and Wetting Phenomena: Drops, Bubbles, Pearls, Waves," Springer Science Business Media, 2013, pp. 1-149.
Gibbs et al., "Encapsulation in the Food Industry: A Review," International Journal of Food Sciences and Nutrition, May 1999, vol. 50(3), pp. 213-224.
Gullapalli., "Soft Gelatin Capsules (softgels)", Journal of Pharmaceutical Sciences, 2010, vol. 99(10), pp. 4107-4148.
Hendrix et al., "Universal Mechanism for Air Entrainment During Liquid Impact," Journal of Fluid Mechanics, Feb. 2016, pp. 1-15.
Jones et al., "The Sounds of Splashes", Science, 1920, vol. 52(1343), pp. 295-296.
Josserand et al.," Droplet Splashing on a Thin Liquid," Physics of Fluids, 2003, vol. 15, pp. 1650-1657.
Kim et al., "Fabrication of Monodisperse Gel Shells and Functional Microgels in Microfluidic Devices, " Angewandte Chemie, 2007, vol. 46(11), pp. 1819-1822.
King et al., "Elastic Sheet on a Liquid Drop Reveals Wrinkling and Crumpling as Distinct Symmetry-Breaking Instabilities," Proceedings of the National Academy of Sciences of the United States of America, Jun. 2012, vol. 109 (25), pp. 9716-9720.
King et al., "Encapsulation and Controlled Release of Food Ingredients, "American Chemical Society, 1995, vol. 3, pp. 26-39.
Lakkis et al., "Encapsulation and Controlled Release Technologies in Food Systems, "Wiley Online Second Edition Library, 2016, pp. 41-377.
Lee, et al.,"New Drop Weight Analysis for Surface Tension Determination of Liquids", Colloids and Surfaces, 2009, Vol. (2-3), pp. 112-120.
Lhuissier et al., "Drop Fragmentation at Impact onto a Bath of an Immiscible Liquid," Physical Review Letters, Jun. 2013, vol. 110, p. 264503-1-264503-5.
Li., et al., "UV Curing for Encapsulated Aroma Nish on Cotton," The Journal of The Textile Institute, 2005, vol. 96, pp. 407-411.
Luo et al., "Electrostatic-Driven Dynamic Jamming of 2D Nanoparticles at Interfaces for Controlled Molecular Diffusion," Angewandte Chemie, 2018, vol. 130, pp. 1-7.
Mitra et al., "Understanding the Early Regime of Drop Spreading," Langmuir, 2016, vol. 32, pp. 8843-8848.

(56) References Cited

OTHER PUBLICATIONS

Mitra et al., "Wetting Characteristics of Underwater Micro-Patterned Surfaces," RSC Advances, Jan. 2017, vol. 7, pp. 9064-9072.
Nedovica et al., "An Overview of Encapsulation Technologies for Food Applications," Procedia Food Science, 2011, vol. 1, pp. 1806-1815.
Oguz et al., "Bubble Entrainment by the Impact of Drops on Liquid Surfaces," Journal of Fluid Mechanics, 1990, vol. 219, pp. 143-179.
Onder et al., "Encapsulation of Phase Change Materials by Complex Coacervation to Improve Thermal Performances of Woven Fabrics", Thermochimica Acta, 2008, vol. 467, pp. 63-72.
Paulsen et al., "Optimal Wrapping of Liquid Droplets With Ultrathin Sheets", Nature Materials, 2015, vol. 14(12), pp. 1206-1209.
Prosperetti A., et al., "The Impact of Drops on Liquid Surfaces and the Underwater Noise of Rain," Annual Review of Fluid Mechanics, 1993, vol. 25, pp. 577-602.
Py et al., "Capillary Origami: Spontaneous Wrapping of a Droplet with an Elastic Sheet," Physical Review Letters, Apr. 2007, vol. 98, pp. 1-5.
Raman et al., "On the Sounds of Splashes," Philosophical Magazine Series 6, Jan. 1920, vol. 39(229), pp. 145-147.
Sahoo et al., "Development of Dual-Phobic Surfaces: Superamphiphobicity in Air and Oleophobicity Underwater," ACS Sustainable Chemistry Engineering, 2017, vol. 5, pp. 6716-6726.
Sebilleau et al., "Equilibrium Thickness of Large Liquid Lenses Spreading Over Another Liquid Surface", Langmuir, 2013, vol. 29(39), pp. 12118-12128.
Singh et al., "Microencapsulation: A Promising Technique for Controlled Drug Delivery," Research in Pharmaceutical Sciences, Oct. 2010, vol. 5(2), pp. 65-77.
Soest et al., "Encapsulation of Fragrances and Flavours: a Way to Control Odour and Aroma in Consumer Products," Encapsulation of Fragrances and Flavours, 2007, pp. 439-455.
Tran et al., "Air Entrainment during Impact of Droplets on Liquid Surfaces," Journal of Fluid Mechanics, 2013, vol. 726, pp. R3-1-R3-11.
Truscott et al., "Unsteady Forces on Spheres during Free-Surface Water Entry," Journal of Fluid Mechanics, Aug. 2012, vol. 704, pp. 173-210.
Utada et al., "Dripping to Jetting Transitions in Coflowing Liquid Streams," Physical Review Letters, Aug. 2007, vol. 99(9), pp. 094502-1-094502-4.
Utada et al.," Dripping, Jetting, Drops, and Wetting: the Magic of Microfluidics," MRS Bull, 2007, vol. 32(9), pp. 702-708.
Voinov et al., "Hydrodynamics of Wetting, "Fluid Dynamics 1976, vol. 11, pp. 714-721.
Waghmare et al., "Under-Water Superoleophobic Glass: Unexplored Role of the Surfactant-Rich Solvent," Scientific Reports, Jul. 2013, vol. 3, pp. 1-7.
Waghmare et al., "Under-Water Superoleophobicity of Fish Scales," Scientific Reports, Jul. 2014, vol. 4, pp. 1-5.

\* cited by examiner

LIQUID ENCAPSULATION METHOD AND COMPOSITIONS AND USES RELATED THERETO

CROSS REFERENCE TO RELATED APPLICATION

This application is a 371 national stage application based on International Patent Application No: PCT/CA2020/050222, filed Feb. 20, 2021, which claims priority to Indian Provisional Patent Application No. 201911006813, filed Feb. 21, 2019, and United States Provisional Patent Application number U.S. 62/906,540, filed Sep. 26, 2019, the entire contents of which are hereby incorporated by reference.

FIELD

The present disclosure relates generally to methods of encapsulating materials and to encapsulated materials produced by such methods. More particularly, the present disclosure relates to liquid encapsulation methods and compositions and uses related thereto.

INTRODUCTION

The following introduction is intended to introduce the reader to this specification but not to define or limit any invention. One or more inventions may reside in a combination or sub-combination of elements or steps described below or in other parts of this document. The inventors do not waive or disclaim their rights to any invention or inventions disclosed in this specification merely by not describing such other invention or inventions in the claims.

Encapsulation bears practical significance in a broad range of industries and applications, including but not limited to the pharmaceutical, agriculture, aquaculture, food and beverage, cosmetics, perfume and personal care industries. In general, encapsulation produces a protective outer layer around a core material. This can be beneficial for a variety of reasons, for example, to safeguard an unstable component from an aggressive or incompatible environment, or to protect a reactive or degradable component for a period of time or until it has reach a desired destination, such as in drug delivery applications.

With respect to encapsulation of liquid core materials, such protection has predominantly been achieved by creating a thin coating layer engulfing a liquid core (e.g. utilizing nano-particles/surfactants/powders) or by wrapping a liquid core material in a thin bendable solid polymer sheet. Among the class of techniques that involve particles, interfacial jamming utilizes the thermodynamically favorable tendency of functionalized nanoparticle surfactants to self-assemble at the interface. Controlled electrical actuation of this interfacial adsorption results in jamming of nanoparticles at the interface leading to formation of an encapsulation structure. Another method involves individual coating of droplets with hydrophobic particles to form so-called "liquid marbles" synthesized by making the core droplet roll on top of a hydrophobic powder layer. Generating such liquid marbles requires considerable manual handling and this method loses feasibility when the core and the surrounding medium are not internally compatible (e.g. miscible/reactive). These methods either require precise manipulation of the constitution and the resulting electrochemistry in the colloidal phase on a case-by-case basis or demand extensive manual handling. Another group of methods from the same category involves formation of an armour of granular particlest 2 around the core droplet resulting from gravity driven destabilization and consequent collapse of a cargo of dense hydrophobic granular particles suspended in an oil layer. However, because of its extensive dependence on gravity driven collapse of the intermediate oil layer (due to the weight of either the core drop or the granular particles forming the shell) the method appears to have an intrinsic restriction in regard to the minimum permissible volume of core drop and thickness and weight of the encapsulation layer. Although it offers some potential for applications such as oil-water separation/spillage control, acceptability in pharmaceutical/food-processing operations remain under question because of the lack of precise control and the involvement of dense granular particles.

The class of methods involving polymeric sheets 3 utilizes the interaction between elasticity and capillarity to spontaneously form a thin polymeric shell membrane around the core droplets. Recently Kumar et al. 3 reported a method where they use the fast dynamics of impact with a floating thin polymeric sheet (thickness range: 46-372 nm) to create a consistent wrapping layer around oil droplets. However, one of the fundamental issues with such methods involving polymeric sheets is the associated technological challenges in the fabrication of ultrathin sheets from the bulk components with controllable precision in micro/nanometer scale.

In this context, liquid-liquid encapsulation has been explored as having potential to circumvent the aforementioned challenging fabrication protocol and potential to provide enhanced dosage efficiency due in part to higher bio-availability of liquid "wrappers" in comparison to their solid/semi-solid counterparts. However, scientific endeavour in this regard is relatively scarce. Loscertales et al. 4 demonstrated a method of generating monodispersed compound droplets by encapsulating a liquid droplet within another liquid shell via electrohydrodynamic actuation of coaxial jet breakup. Their method poses a rather stringent restriction on the choice of liquids, which not only demands a higher liquid-dielectric surface tension of the core liquid in comparison to that of the outer shell but also requires one of the liquids to be electrically conducting. Utada et al. 5 utilized double emulsion formation in a microcapillary device to obtain monodispersed encapsulated droplets. However, ensuring monodispersity and structural consistency of the resulting droplets requires precision control of the jet breakup mechanism and the applicability of the method appears to be restricted to the microfluidic scale.

New and effective techniques for encapsulating core materials, including liquid encapsulation techniques, are desirable.

SUMMARY

It is an object of the present disclosure to provide a new technique for liquid encapsulation of a core material, including but not limited to a liquid core material, and to provide compositions and uses related thereto.

In one aspect of the present disclosure, there is provided a method of forming an encapsulated core material, the method comprising providing an interfacial fluid and providing a host fluid, the interfacial fluid being layered on the host fluid; and passing a core material having sufficient kinetic energy through the interfacial fluid and into the host fluid such that the interfacial fluid forms a shell around the core material, thereby forming the encapsulated core material.

In another aspect of the present disclosure, there is provided a method of forming a multi-layered encapsulated core material comprising a core material and a shell, the method comprising: providing an interfacial fluid layer and a host fluid, the interfacial fluid layer comprising at least a first and a second interfacial fluid, the first interfacial fluid being layered on the second interfacial fluid and the second interfacial fluid being layered on the host fluid; and passing a core material having sufficient kinetic energy through the interfacial fluid layer and into the host fluid such that the interfacial fluid layer forms a shell around the core material, the shell comprising the at least first and second interfacial fluid, thereby forming the multi-layered encapsulated core material.

In an embodiment of any one of the preceding aspects, there is provided a method wherein the core material has a density $p_1$, the interfacial fluid has a density $p_2$, the host fluid has a density $p_3$, and wherein $p_2 < p_3 < p_1$. In another embodiment of any one of the preceding aspects, there is provided a method wherein the core material has a density $p_1$, the interfacial fluid has a density $p_2$, the host fluid has a density $p_3$, and wherein $p_1 > p_2 > p_3$.

In an embodiment of any one of the preceding aspects, optionally in combination with one or more of the preceding embodiments, there is provided a method wherein providing the interfacial fluid layered on the host fluid comprises providing a volume V of the interfacial fluid.

In an embodiment of any one of the preceding aspects, optionally in combination with one or more of the preceding embodiments, there is provided a method wherein the volume V is selected to provide the interfacial fluid layered on the host fluid. For example, the density of the interfacial layer may be less than the density of the host fluid, thereby providing the interfacial fluid layered on the host fluid. For sufficiently small volumes V of the interfacial fluid, the density of the interfacial fluid may be greater than the density of the host fluid. For example, if a heavier fluid is dispensed on top of a lighter fluid at a very slow flow rate and from close vicinity (so that kinetic energy at point of contact is minimal), then it can be possible to stably hold a heavier fluid atop a lighter fluid (i.e., provide the interfacial fluid layered on the host fluid). However, for higher volumes V, the interfacial fluid would destabilize and sink; and as such, encapsulation with heavier interfacial fluids is only possible if the volume V is sufficiently low.

In an embodiment of any one of the preceding aspects, optionally in combination with one or more of the preceding embodiments, there is provided a method wherein the shell has a thickness T and modifying the volume V adjusts the thickness T. For example, the thickness of the shell of the encapsulated core material can be tuned, or varied by changing the thickness of the layer of interfacial fluid prior to passing the core material therethrough.

In an embodiment of any one of the preceding aspects, optionally in combination with one or more of the preceding embodiments, there is provided a method wherein providing the interfacial fluid layered on the host fluid comprises dispensing the interfacial fluid on top of the host fluid.

In an embodiment of any one of the preceding aspects, optionally in combination with one or more of the preceding embodiments, there is provided a method wherein dispensing comprises using a syringe pump and needle assembly, a rotary, or an electrical actuator to dispense the interfacial fluid on top of the host fluid.

In an embodiment of any one of the preceding aspects, optionally in combination with one or more of the preceding embodiments, there is provided a method wherein the core material is a fluid. In an embodiment of any one of the preceding aspects, optionally in combination with one or more of the preceding embodiments, there is provided a method further comprising forming the core material, wherein the core material is a core droplet. In an embodiment of any one of the preceding aspects, optionally in combination with one or more of the preceding embodiments, there is provided a method wherein forming the core droplet comprises dispensing the fluid from a syringe pump and needle assembly.

In an embodiment of any one of the preceding aspects, optionally in combination with one or more of the preceding embodiments, there is provided a method wherein passing the core material comprises dropping the core material from a height H from the interfacial fluid. In an embodiment of any one of the preceding aspects, optionally in combination with one or more of the preceding embodiments, there is provided a method wherein dropping the core material comprises imparting a first kinetic energy $We_i$ to the core material.

In an embodiment of any one of the preceding aspects, optionally in combination with one or more of the preceding embodiments, there is provided a method wherein:

$$H > \frac{3(\gamma_{12} + \gamma_{23} - \gamma_1)}{\rho_1 g R_c},$$

where g is gravitational acceleration, $R_c$ is radius of the core material assuming spherical geometry, $p_1$ is density of the core material, $y_{12}$ is core material/interfacial fluid interfacial tension, $y_{23}$ is interfacial fluid/host fluid interfacial tension, and $y_1$ is air/core material interfacial tension.

In an embodiment of any one of the preceding aspects, optionally in combination with one or more of the preceding embodiments, there is provided a method wherein:

$$We_i = \frac{\rho_1 v^2 l_c}{\gamma_1} \approx \frac{2\rho_1 g H l_c}{\gamma_1}$$

where v is velocity of the core material immediately before impacting the interfacial fluid, g is acceleration due to gravity, $p_1$ is density of the core material, $l_c$ is characteristic length scale typically expressed as radius of the core material assuming spherical shape, H is impact height, and $y_1$ is air/core material interfacial tension.

In an embodiment of any one of the preceding aspects, optionally in combination with one or more of the preceding embodiments, there is provided a method wherein passing the core material comprises actuating the core material from a distance D from the interfacial fluid. In an embodiment of any one of the preceding aspects, optionally in combination with one or more of the preceding embodiments, there is provided a method wherein actuating the core material comprises imparting a second kinetic energy $We$ to the core material.

In an embodiment of any one of the preceding aspects, optionally in combination with one or more of the preceding embodiments, there is provided a method wherein actuating comprises accelerating the core material droplet using pressure, jetting, electrostatic interactions, electrohydrodynamic actuation, or a centripetal force. For example, an adverse viscous energy barrier to encapsulation of a core material may be mitigated by suitably compensating the kinetic energy of a core droplet (e.g. by increasing impact height or by providing acceleration by other means—jetting/electrohydrodynamic actuation).

In an embodiment of any one of the preceding aspects, optionally in combination with one or more of the preceding embodiments, there is provided a method wherein the core material is a solid. In an embodiment of any one of the preceding aspects, optionally in combination with one or more of the preceding embodiments, there is provided a method further comprising providing the core material, wherein the core material is a core solid.

In an embodiment of any one of the preceding aspects, optionally in combination with one or more of the preceding embodiments, there is provided a method wherein, when passing the core material, the only fluid the core material contacts is the interfacial fluid. In an embodiment of any one of the preceding aspects, optionally in combination with one or more of the preceding embodiments, there is provided a method wherein forming the encapsulated core material comprises protecting the core material with the shell.

In an embodiment of any one of the preceding aspects, optionally in combination with one or more of the preceding embodiments, there is provided a method wherein protecting the core material comprises preventing the core material from contacting the host fluid. In an embodiment of any one of the preceding aspects, optionally in combination with one or more of the preceding embodiments, there is provided a method wherein the core material and the host fluid are incompatible. In an embodiment of any one of the preceding aspects, optionally in combination with one or more of the preceding embodiments, there is provided a method wherein the core material is miscible with the host fluid. In an embodiment of any one of the preceding aspects, optionally in combination with one or more of the preceding embodiments, there is provided a method wherein the core material is reactive with the host fluid.

In an embodiment of any one of the preceding aspects, optionally in combination with one or more of the preceding embodiments, there is provided a method wherein the core material, the interfacial fluid, or the host fluid comprise an additive. In an embodiment of any one of the preceding aspects, optionally in combination with one or more of the preceding embodiments, there is provided a method wherein the additive is a pharmaceutical compound, an enzyme, a microparticle, a nanoparticle, a surfactant, a mineral, a nutrient, an oil, a fish oil, a probiotic, a polymer, a water-treatment compound, or a soil-treatment compound. In an embodiment of the preceding embodiment, the additive is in a fluid phase (i.e., the core material, interfacial fluid, and host fluid are all fluids) to facilitate absorption into a subject's blood stream. In another embodiment of the preceding embodiment, the additive is in a fluid phase (i.e., the core material, interfacial fluid, and host fluid are fluids) to facilitate biodegradability. In an embodiment of any one of the preceding aspects, optionally in combination with one or more of the preceding embodiments, there is provided a method wherein the additive is a pharmaceutical compound.

In an embodiment of any one of the preceding aspects, optionally in combination with one or more of the preceding embodiments, the encapsulated core material comprises a condensed phase, such as a liquid, solid, or a combination there of. In an embodiment of any one of the preceding aspects, optionally in combination with one or more of the preceding embodiments, there is provided a method wherein, when the core material is a fluid, the fluid is a liquid, a liquid mixture, a solution, a suspension, a liquid polymer, or a liquid polymer mixture. For example, when the core material is a fluid, the fluid may comprise any one or a combination of: a solid suspension, an additive, a microparticle, microparticles, a nanoparticle, nanoparticles, a surfactant, food nutrients, an Omega oil, a fish oil, a probiotic, or a polymer.

In an embodiment of any one of the preceding aspects, optionally in combination with one or more of the preceding embodiments, there is provided a method wherein the fluid is a laser liquid. In an embodiment of any one of the preceding aspects, optionally in combination with one or more of the preceding embodiments, there is provided a method wherein the laser liquid is a mixture of silicones and polyphenol ethers.

In an embodiment of any one of the preceding aspects, optionally in combination with one or more of the preceding embodiments, there is provided a method wherein, when the core material is a solid, the solid is a polymer, a nut, or a seed.

In an embodiment of any one of the preceding aspects, optionally in combination with one or more of the preceding embodiments, there is provided a method wherein the interfacial fluid is a liquid, such as a liquid mixture, an oil, a solution, a suspension, a liquid polymer, a liquid polymer mixture, a liquid agar gel, a liquid gelatin, or a liquid cellulose. In an embodiment of any one of the preceding aspects, optionally in combination with one or more of the preceding embodiments, there is provided a method wherein the interfacial fluid is a canola oil, a silicone oil, hydroxypropylmethylcellulose, or hexanes.

In an embodiment of any one of the preceding aspects, optionally in combination with one or more of the preceding embodiments, there is provided a method wherein the host fluid is a liquid, a liquid mixture, a solution, a suspension, a liquid polymer, a liquid polymer mixture, a liquid agar gel, a liquid gelatin, or a liquid cellulose. In an embodiment of any one of the preceding aspects, optionally in combination with one or more of the preceding embodiments, there is provided a method wherein the host fluid is water.

In an embodiment of any one of the preceding aspects, optionally in combination with one or more of the preceding embodiments, there is provided a method wherein forming the encapsulated core material further comprises hardening the core material or the shell.

In an embodiment of any one of the preceding aspects, optionally in combination with one or more of the preceding embodiments, there is provided a method wherein hardening the core material or the shell comprises curing the core material to form a hardened core material, or curing the shell to form a hardened shell. In an embodiment of any one of the preceding aspects, optionally in combination with one or more of the preceding embodiments, there is provided a method wherein curing the shell comprises exposing the core material or the shell to ultraviolet radiation. In an embodiment of any one of the preceding aspects, optionally in combination with one or more of the preceding embodiments, there is provided a method wherein curing the shell comprises triggering a coacervate formation. In an embodiment of any one of the preceding aspects, optionally in combination with one or more of the preceding embodiments, there is provided a method wherein curing the shell comprises exposing the shell to heat.

In an embodiment of any one of the preceding aspects, optionally in combination with one or more of the preceding embodiments, there is provided a method further comprising enclosing the encapsulated core material. In an embodiment of any one of the preceding aspects, optionally in combination with one or more of the preceding embodiments, there is provided a method wherein enclosing the encapsulated core material comprises enclosing the encapsulated core material with a polymer sheet or an interfacial assembly of particles.

In another aspect of the present disclosure, there is provided an encapsulated core material composition, comprising a host fluid; and an encapsulated core material in the host fluid, the encapsulated core material comprising a core material and an interfacial fluid, the interfacial fluid encapsulating the core material with a shell.

In an embodiment of the preceding aspect, there is provided a composition wherein the core material has a density $p_1$, the interfacial fluid has a density $p_2$, the host fluid has a density $p_3$, and wherein $p_2 < p_3 < p_1$. In an embodiment of the preceding aspect, there is provided a composition wherein the core material has a density $p_1$, the interfacial fluid has a density $p_2$, the host fluid has a density $p_3$, and wherein $p_1 > p_2 > p_3$. In an embodiment of the preceding aspect, optionally in combination with one or more of the preceding embodiments, there is provided a composition wherein the shell has a thickness T.

In an embodiment of the preceding aspect, optionally in combination with one or more of the preceding embodiments, there is provided a composition wherein, for the encapsulated core material in the host fluid, $$Y_{13} > Y_{12} + Y_{23}$$

where $y_{13}$ is core material/host fluid interfacial tension, $y_{12}$ is core material/interfacial fluid interfacial tension, and $y_{23}$ is interfacial fluid/host fluid interfacial tension.

In an embodiment of the preceding aspect, optionally in combination with one or more of the preceding embodiments, there is provided a composition wherein the shell protects the core material from the host fluid. In an embodiment of the preceding aspect, optionally in combination with one or more of the preceding embodiments, there is provided a composition wherein the shell prevents the core material from contacting the host fluid. In an embodiment of the preceding aspect, optionally in combination with one or more of the preceding embodiments, there is provided a composition wherein the core material and the host fluid are incompatible. In an embodiment of the preceding aspect, optionally in combination with one or more of the preceding embodiments, there is provided a composition wherein the core material is miscible with the host fluid. In an embodiment of the preceding aspect, optionally in combination with one or more of the preceding embodiments, there is provided a composition wherein the core material is reactive with the host fluid.

In an embodiment of the preceding aspect, optionally in combination with one or more of the preceding embodiments, there is provided a composition wherein the core material, the interfacial fluid, or the host fluid comprise an additive. In an embodiment of the preceding aspect, optionally in combination with one or more of the preceding embodiments, there is provided a composition wherein the additive is a pharmaceutical compound, an enzyme, a microparticle, a nanoparticle, a surfactant, a mineral, a nutrient, an oil, a fish oil, a probiotic, a polymer, a water-treatment compound, or a soil-treatment compound. In an embodiment of the preceding embodiment, the additive is in a fluid phase (i.e., the core material, interfacial fluid, and host fluid are all fluids) to facilitate absorption into a subject's blood stream. In another embodiment of the preceding embodiment, the additive is in a fluid phase (i.e., the core material, interfacial fluid, and host fluid are all fluids) to facilitate biodegradability. In an embodiment of any one of the preceding aspects, optionally in combination with one or more of the preceding embodiments, there is provided a composition wherein the additive is a pharmaceutical compound.

In an embodiment of the preceding aspect, optionally in combination with one or more of the preceding embodiments, there is provided a composition wherein the core is a solid. In an embodiment of the preceding aspect, optionally in combination with one or more of the preceding embodiments, there is provided a composition wherein the solid is a polymer, a nut, or a seed.

In an embodiment of the preceding aspect, optionally in combination with one or more of the preceding embodiments, there is provided a composition wherein the core material is a fluid. In an embodiment of the preceding aspect, optionally in combination with one or more of the preceding embodiments, there is provided a composition wherein the core fluid is a liquid, a liquid mixture, a solution, a suspension, a liquid polymer, or a liquid polymer mixture. For example, when the core material is a fluid, the fluid may comprise any one or a combination of: a solid suspension, an additive, a microparticle, microparticles, a nanoparticle, nanoparticles, a surfactant, food nutrients, an Omega oil, a fish oil, a probiotic, or a polymer. In an embodiment of the preceding aspect, optionally in combination with one or more of the preceding embodiments, there is provided a composition wherein the core fluid a laser liquid. In an embodiment of the preceding aspect, optionally in combination with one or more of the preceding embodiments, there is provided a composition wherein the laser liquid is a mixture of silicones and polyphenol ethers.

In an embodiment of the preceding aspect, optionally in combination with one or more of the preceding embodiments, there is provided a composition wherein the interfacial fluid is a liquid, a liquid mixture, an oil, a solution, a suspension, a liquid polymer, a liquid polymer mixture, a liquid agar gel, a liquid gelatin, or a liquid cellulose. In an embodiment of the preceding aspect, optionally in combination with one or more of the preceding embodiments, there is provided a composition wherein the interfacial fluid is a canola oil, a silicone oil, hydroxypropylmethylcellulose, or hexanes.

In an embodiment of the preceding aspect, optionally in combination with one or more of the preceding embodiments, there is provided a composition wherein the host fluid is a liquid, a liquid mixture, a solution, a suspension, a liquid polymer, a liquid polymer mixture, a liquid agar gel, a liquid gelatin, or a liquid cellulose. In an embodiment of the preceding aspect, optionally in combination with one or more of the preceding embodiments, there is provided a composition wherein the host fluid is water.

In an embodiment of the preceding aspect, optionally in combination with one or more of the preceding embodiments, there is provided a composition wherein the shell is a hardened shell. In an embodiment of the preceding aspect, optionally in combination with one or more of the preceding embodiments, there is provided a composition wherein the hardened shell comprises a crosslinked interfacial fluid. In an embodiment of the preceding aspect, optionally in combination with one or more of the preceding embodiments, there is provided a composition wherein the hardened shell comprises a coacervate formation formed from the interfacial fluid.

In an embodiment of the preceding aspect, optionally in combination with one or more of the preceding embodiments, there is provided a composition further comprising an enveloping layer enclosing the encapsulated core material. In an embodiment of the preceding aspect, optionally in combination with one or more of the preceding embodiments, there is provided a composition wherein the enveloping layer comprises a polymer sheet or an interfacial assembly of particles.

In an embodiment of the preceding aspect, optionally in combination with one or more of the preceding embodiments, there is provided a composition wherein the shell comprises at least a first and a second interfacial fluid, and the core material is encapsulated with a first shell formed from the first interfacial fluid, and the first shell is encapsulated with a second shell formed from the second interfacial fluid.

In another aspect of the present disclosure, there is provided a use of the encapsulated core material made by the method described herein, or the composition described herein for delivery of a pharmaceutical compound. In another aspect of the present disclosure, there is provided a use of the encapsulated core material made by the method described herein, or the composition described herein for delayed release of a pharmaceutical compound.

In another aspect of the present disclosure, there is provided a use of the encapsulated core material made by the method described herein, or the composition described herein in a cosmetic product. In another aspect of the present disclosure, there is provided a use of the encapsulated core material made by the method described herein, or the composition described herein for delayed release of an additive in a cosmetic product.

In another aspect of the present disclosure, there is provided a use of the encapsulated core material made by the method described herein, or the composition described herein in an emulsion.

In another aspect of the present disclosure, there is provided a use of the encapsulated core material made by the method described herein, or the composition described herein for encapsulating a food product. In another aspect of the present disclosure, there is provided a use of the encapsulated core material made by the method described herein, or the composition described herein in a food product. In an embodiment of any one of the preceding aspects, there is provided a use wherein the food product is a beverage, a nutraceutical, a confectionary, a fish oil, an omega 3 fatty acid, a seed, a nut, or a probiotic. For example, seeds or nuts may be a core material of the encapsulated core material, wherein being encapsulated by a shell of interfacial fluid protects the seed or nut from oxidation.

In another aspect of the present disclosure, there is provided a kit comprising a host fluid, an interfacial fluid, and a core, and instructions for use thereof. In an embodiment of the preceding aspect, there is provided a kit further comprising an additive and instructions for adding the additive to any one of the core material, the interfacial fluid, or the host fluid.

In another aspect of the present disclosure, there is provided a kit comprising a host fluid, a encapsulated core material in the host fluid, and instructions for use thereof. In an embodiment of the preceding aspect, there is provided a kit further comprising an additive and instructions for adding the additive to any one of the encapsulated core material, or the host fluid. In an embodiment of any one of the preceding aspects, optionally in combination with one or more of the preceding embodiments, there is provided a kit wherein the additive is a pharmaceutical compound, an enzyme, a microparticle, a nanoparticle, a surfactant, a mineral, a nutrient, an oil, a fish oil, a probiotic, a polymer, a water-treatment compound, or a soil-treatment compound.

In an embodiment of the preceding embodiment, the additive is in a fluid phase (i.e., the core material, interfacial fluid, and host fluid are all fluids) to facilitate absorption into a subject's blood stream. In another embodiment of the preceding embodiment, the additive is in a fluid phase (i.e., the core material, interfacial fluid, and host fluid are all fluids) to facilitate biodegradability. In an embodiment of any one of the preceding aspects, optionally in combination with one or more of the preceding embodiments, there is provided a kit wherein the additive is a pharmaceutical compound.

Other aspects and features of the present disclosure will become apparent to those ordinarily skilled in the art upon review of the following description of specific embodiments in conjunction with the accompanying figures.

BRIEF DESCRIPTION OF THE FIGURES

Embodiments of the present disclosure will now be described, by way of example only, with reference to the attached Figures.

DETAILED DESCRIPTION

Figure 1:
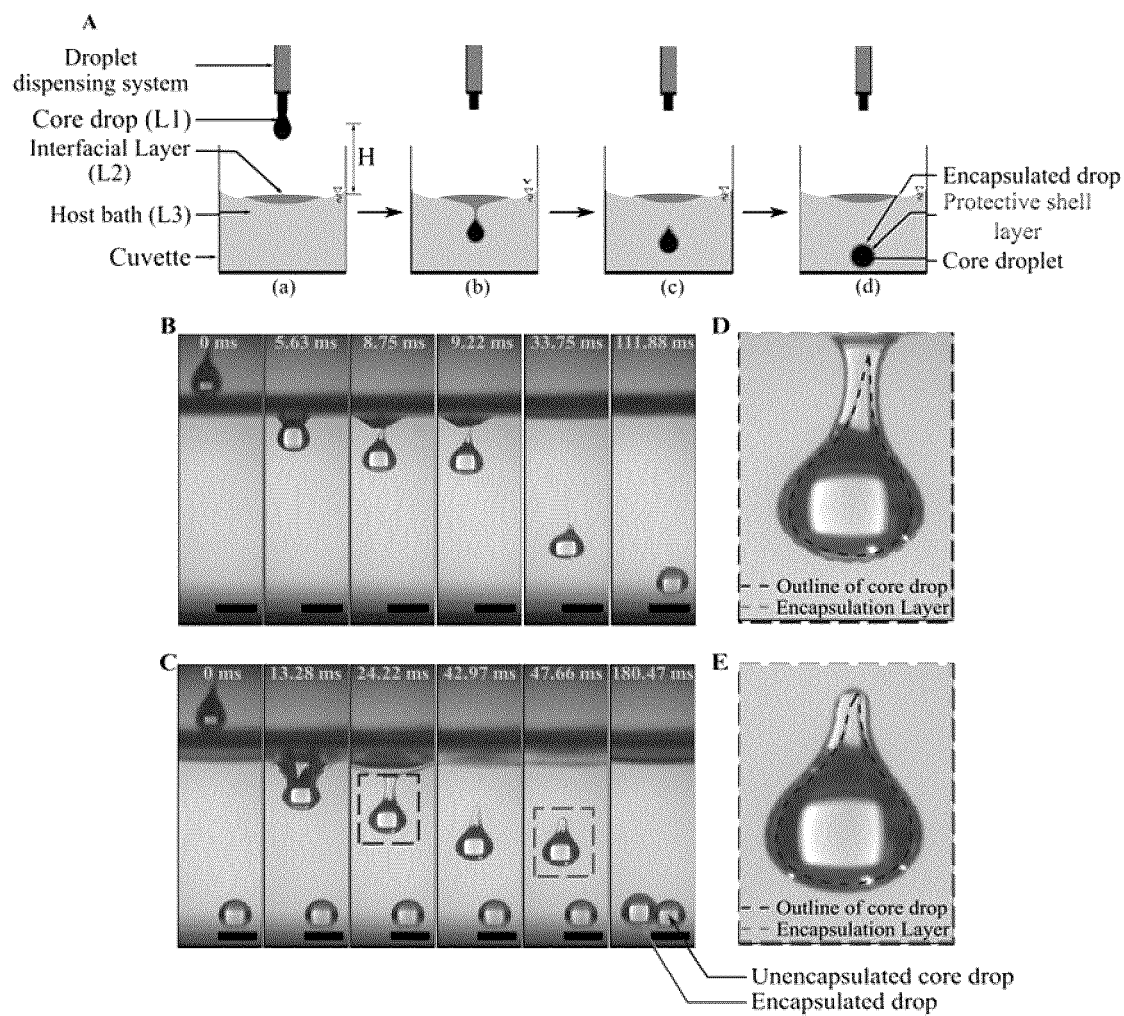
FIG. 1 depicts a process leading to liquid-liquid encapsulation and visual characterization of encapsulation layer. (A) Step-by-step schematic representation (not to scale) of the encapsulation process. (B) Time series demonstrating interfacial phenomena of entry of a core droplet (consisting of liquid L1, here laser oil) inside liquid bath L3 (here water) when there was no interfacial film (or layer) (i.e., absence of liquid L2) and therefore no encapsulation. Here impact height, H=6.5 cm (C) Time series illustrating encapsulation process in the same experimental set up as (B) after a thin interfacial film (or layer) (here L2 was canola oil) of volume $V_{film}$=350 µL has been dispensed on top of the host water bath. The fourth time stamp denotes successful shell formation and therefore completion of encapsulation process, with the required time being 42.97 ms. (D) Zoomed in view of the formation process of the shell layer (made of the interfacial liquid L2), the region of interest is highlighted on the corresponding time snap T=24.22 ms in time series (C) by a dotted square.. (E) Zoomed in view of an encapsulated drop corresponding to the region of interest highlighted by another dotted square on time snap T=47.66 ms in (C), with distinctively identifiable outlines of the core and shell. The scale bar represents 4 mm wherever applicable throughout the figure.

Generally, the present disclosure relates to liquid encapsulation methods, encapsulated core materials produced by these methods, and uses of the encapsulated core materials. By liquid encapsulation, it is meant that a core material, such as a liquid, solid or semi-solid core material, is encapsulated in a liquid shell. This is accomplished, in general, by providing an interfacial fluid that acts as a barrier between the core material and a host fluid and passing the core material through the interfacial layer and into the host fluid. The core material is imparted with sufficient energy, e.g. kinetic energy or force, to pass through the interfacial fluid and into the host fluid. As the core material moves into the host fluid, a shell comprised of interfacial fluid is formed around the core material. This results in the formation of an encapsulated core material in the host fluid. The encapsulated core material may remain in the host fluid for use, or may be subjected to further treatment steps prior to use. A skilled person will appreciate that the liquid encapsulation methods of the present disclosure, and the products produced thereby, have many practical applications, including but not limited to carrying and/or delivering an additive of interest, such as an active ingredient or payload.

In an aspect of the present disclosure, there is provided a method of forming an encapsulated core material, i.e. a liquid-encapsulated core material. The method comprises providing an interfacial fluid and a host fluid. The interfacial fluid is provided between the core material and the host fluid. It will be noted that the terms liquid and fluid are used substantially interchangeably herein to refer to flowable materials. The term material is used substantially interchangeably with substance or composition in that a material may comprise one or more components. The interfacial fluid and the host fluid are selected relative to each other such that the interfacial fluid is capable of being layered on the host fluid. Any suitable means of layering may be utilized. Layering may occur naturally due to the physicochemical properties of the interfacial fluid and the host fluid and/or may be facilitated through layering techniques know to those skilled in the art. In accordance with embodiments of the disclosure, a selected core material is passed through the interfacial fluid with sufficient energy to enter into the host fluid. The core material and the interfacial fluid are selected relative to each other such that, as the core material passes through the interfacial fluid and into the host fluid, the interfacial fluid forms a liquid shell around the core material, thereby encapsulating the core material to form an encapsulated core material, e.g. a liquid-encapsulated core material, in the host fluid. The host fluid may comprise one or multiple units of the encapsulated core material. The encapsulated core material may take on any suitable size or shape in the host fluid, such as a substantially spherical shape.

The interfacial layer may itself comprise one or more layers. Thus, in certain embodiments, there is provided a method of forming a multi-layered encapsulated core material comprising a core material and a shell, the method comprising: providing an interfacial fluid layer and a host fluid, the interfacial fluid layer comprising at least a first and a second interfacial fluid, the first interfacial fluid being layered on the second interfacial fluid and the second interfacial fluid being layered on the host fluid; and passing a core material having sufficient kinetic energy through the interfacial fluid layer and into the host fluid such that the interfacial fluid layer forms a shell around the core material, the shell comprising the at least first and second interfacial fluid, thereby forming the multi-layered encapsulated core material.

In another an aspect of the disclosure, there is provided an encapsulated core material formed via any one of the methods described throughout the specification, including the examples. The encapsulated core material may be present in the host fluid or may be subjected to further manipulation prior to use. In some embodiments, the encapsulated core material may be isolated, or transferred from the host fluid, utilizing techniques known to those of skill in the art. For example, the encapsulated core material may be transferred from a first host fluid to a second host fluid prior to use, or may be subjected to further process steps, such as isolation, drying, freezing, freeze-drying, functionalization, or labeling, to name but a few.

In another aspect, there is provided an encapsulated core material composition. In some embodiments, the encapsulated core material composition comprises an encapsulated core material, the encapsulated core material comprising a core material and an interfacial fluid, the interfacial fluid encapsulating the core material, e.g. forming a shell. In some embodiments, the encapsulated core material is present in a host fluid. In some embodiments, the encapsulated core material is isolated from the host fluid. In some embodiments, the encapsulated core material composition comprises a host fluid; and an encapsulated core material in the host fluid, the encapsulated core material comprising a core material and an interfacial fluid, the interfacial fluid encapsulating the core material (e.g. forming a shell around the core material).

Figure 3:
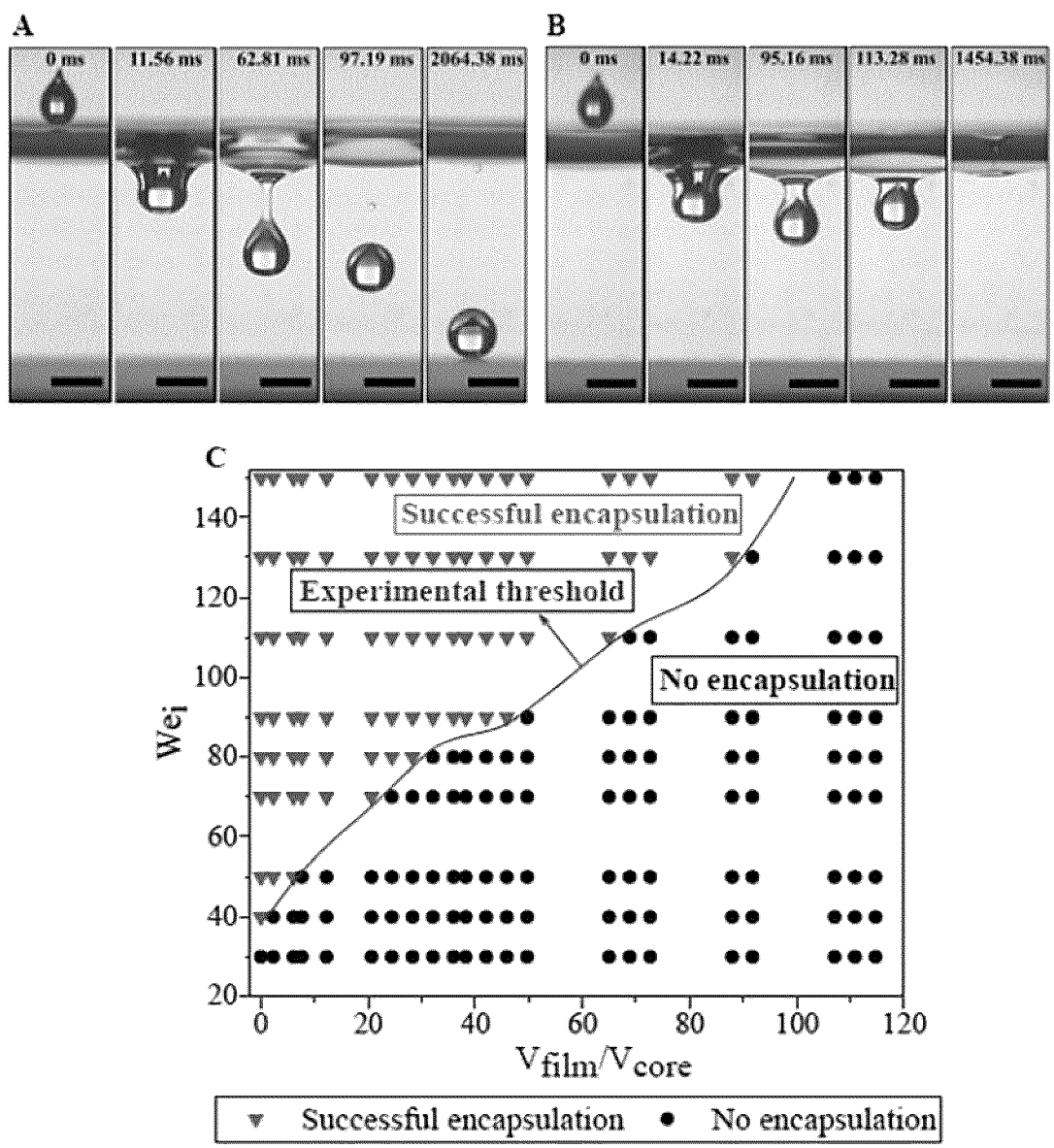
FIG. 3 depicts success of encapsulation: dependence on impact Weber number, Wei and non-dimensionalized interfacial film volume, $V_{film}/V_{core}$. (A) Successful encapsulation: Time series depicting successful encapsulation process for $We_i$=130 and $V_{film}/V_{core}$=87.92. (B) No encapsulation: Time series demonstrating the unsuccessful attempt of the droplet towards encapsulation and consequent entrapment at the interfacial layer for the same impact Weber number, We$_i$=130 but an increased interfacial film volume with V$_{film}$/V$_{core}$=91.74. (C) A regime map demonstrating the dependence of the success of encapsulation process on We$_i$ and V$_{film}$/V$_{core}$. The experimental threshold for the same is illustrated by the zone boundary separating the two regimes—successful encapsulation and no encapsulation.

As used herein, sufficient kinetic energy refers to the core material having sufficient energy (e.g. combination of velocity, mass, density, etc.), to pass through the interfacial fluid into the host fluid. Energy may be imparted onto the core material by any suitable means or force, including but not limited to gravity. The amount of kinetic energy required for a particular core material to pass through the interfacial fluid and into the host fluid will depend on a number of factors and can be determined by persons of skill in the art and having regard to the present disclosure. Factors to consider may include but are not limited to one or combination of: (i) composition, size, mass, shape, viscosity, velocity and/or density of the core material; (ii) composition, density and/or viscosity of the interfacial fluid; or (iii) thickness and/or interfacial energies of the interfacial layer; which are properties that may be known or determined for a particular core material and interfacial fluid (e.g., see Example 1 (for example, Sections—Theoretical criteria governing the formation and stability of encapsulation: an equilibrium thermodynamics perspective; and Role of impact Weber number and interfacial film (or layer) volume on successful encapsulation: deviation from idealized theoretical estimate), FIG. 3, FIG. 14, etc.); and (iv) composition, density and/or viscosity of the host fluid. Thus, sufficient kinetic energy may be determined by a person of skill in the art depending at least on the known or determined properties of the selected core material, interfacial fluid and/or host fluid, their relation to one another, and/or the method steps employed.

A suitable combination of core material, interfacial fluid and host fluid may be selected by a person of skill in the art depending on the particular objective and application. A skilled person, having regard to the present disclosure, will understand that the relative properties of the core material, the interfacial fluid and the host fluid must be considered in selecting a combination that will result in a desired rate of successful encapsulation. As used herein, physicochemically compatible refers to relative properties of two materials in communication with one another (e.g. the core material and the interfacial fluid and/or the interfacial fluid and the host fluid) that permit encapsulation of the core material according to the disclosed methods. For example, two physicochemically compatible materials in communication may be mutually unreactive and/or immiscible. In some embodiments, the core material and the interfacial fluid are physicochemically compatible. In some embodiments, the interfacial fluid and host fluid are physicochemically compatible. In some embodiments, the host fluid and core material are physicochemically compatible. In some embodiments, which may be combined with any of the embodiments described herein, the host fluid and the core material are not physicochemically compatible (i.e. are physicochemically incompatible) in the context of the present disclosure, e.g. they are reactive and/or are miscible relative to one another. "Miscible" or "miscibility" refers to a property of two liquids that when mixed provide a homogeneous solution, or a single phase. In contrast, "immiscible" or "immiscibility"

is a property of two liquids that when mixed provide a heterogeneous mixture, or two distinct phases (i.e., layers). As a skilled person would recognize, this is not meant to imply that combinations of the two liquids will be single-phase mixtures when "miscible", or two-phase mixtures when "immiscible" in all proportions or under all conditions.

In embodiments any of the methods and compositions described herein, any one or more of the host fluid, interfacial fluid, and core material may be an aqueous fluid, a non-aqueous fluid, a polymeric fluid, a hydrophilic fluid, a hydrophobic fluid or an amphiphilic fluid. When comparing two materials to each other, they may be described, for example, as relatively more or less hydrophobic or hydrophilic when compared to a reference fluid. In some embodiments, the host fluid and the core material are a different fluid. In some embodiments, the host fluid and the core material are the same fluid. In other embodiments, the core material may be a solid or semi-solid, and that solid or semi-solid may be hydrophilic, or hydrophobic. In some embodiments, the core material is physicochemically incompatible with the host fluid. In some embodiments, the host fluid comprises an aqueous fluid, the interfacial fluid comprises a non-aqueous fluid, and the core material is physicochemically incompatible with the host fluid. In some embodiments, the host fluid comprises a non-aqueous fluid, the interfacial fluid comprises an aqueous fluid, and the core material is physicochemically incompatible with the host fluid. In some embodiments, the host fluid comprises a hydrophilic fluid, the interfacial fluid comprises a hydrophobic fluid, and the core material is physicochemically incompatible with the host fluid. In some embodiments, the host fluid comprises a hydrophobic fluid, the interfacial fluid comprises a hydrophilic fluid, and the core material is physicochemically incompatible with the host fluid. In some embodiments, the core material is physicochemically compatible with the host fluid but encapsulation is nonetheless desired.

In some embodiments of the methods and compositions described herein, the core material has a density $p_1$, the interfacial fluid has a density $p_2$, the host fluid has a density $p_3$. In some embodiments, $p_2 < p_3 < p_1$. In some embodiments, $p_1 > p_2 > p_3$. Further, the interfacial fluid is capable of being layered on the host fluid. In some examples, the interfacial fluid is layered on the host fluid, for example, by providing a volume V of the interfacial fluid, which is selected to provide the interfacial fluid layered on the host fluid. Said layering may be facilitated due to a difference in hydrophilic/hydrophobic properties of the host fluid and interfacial fluid, a difference in miscibilities of the host fluid and interfacial fluid, a difference in densities, or a difference in surface tensions. In some examples, the interfacial fluid may be layered on the host fluid because the interfacial fluid is hydrophilic and the host liquid is hydrophobic, or vice versa. Alternatively, the interfacial fluid may be layered on the host fluid because the interfacial fluid and the host liquid are immiscible. In other examples, the interfacial fluid may be layered on the host fluid because the interfacial fluid is less dense than the host liquid. For sufficiently small volumes V of the interfacial fluid, the interfacial fluid may be layered on the host fluid even if the density of the interfacial fluid is greater than the density of the host fluid. For example, if a heavier fluid is dispensed on top of a lighter fluid at a very slow flow rate and from close vicinity (so that kinetic energy at point of contact is minimal), then it can be possible to stably hold a heavier fluid atop a lighter fluid (e.g., by relying on surface tensions). However, for higher volumes V, the interfacial fluid may destabilize and sink; and as such, encapsulation with heavier interfacial fluids is possible if the volume V is sufficiently low. A skilled person would appreciate that the volumes that are necessary to facilitate layering depends on the types of interfacial and host fluids that are being used.

In some examples, the interfacial fluid is layered on the host fluid by dispensing the interfacial fluid on top of the host fluid, wherein dispensing comprises using a syringe pump and needle assembly, a rotary, a piezoelectric dispenser, or an electrical actuator to dispense the interfacial fluid on top of the host fluid.

When forming an encapsulated core material, the volume V of interfacial fluid that facilitates a successful encapsulation is, at least in part, dependent on the end use or specific application of the encapsulated material. As is described herein, providing a larger volume V of the interfacial fluid can increase the thickness of the shell that forms around the core material as it is being encapsulated. As will be appreciated by skilled persons, increasing the volume V, may require increasing the amount of kinetic energy that a core material has such that it can successfully pass through the layer of interfacial fluid into the host fluid to be encapsulated (as described above). For example, if $V_1 > V_2$, then the thickness of the shell encapsulating the core material resulting from $V_1$ will be greater than the thickness of the shell encapsulating the core material resulting from $V_2$; and the kinetic energy needed to pass the core material through volume $V_1$ of interfacial fluid will be greater than the kinetic energy needed to pass the core material through volume $V_2$ of interfacial fluid (e.g., see Example 1, Section—Confirmation of stability and integrity of encapsulation & the dependence on interfacial film volume; FIG. 4).

Optimal ranges of volume V may be selected by a person of skill in the art depending on the desired application or end use of the encapsulated material. In some examples, volume V is in a range of about 0.1 mL to about 10 mL; or in a range of 0.1 mL to about 100 mL. Smaller or larger volumes are of course possible and can be suitably selected by persons of skill in the art depending on the application, objective and scale.

The shell of the encapsulated core material has a thickness T and modifying the volume V adjusts said thickness. For example, the thickness of the shell of the encapsulated core material can be tuned, or varied by changing the thickness of the layer of interfacial fluid prior to passing the core material therethrough. As described above, providing a larger volume V of the interfacial fluid can increase the thickness T of the shell that forms around the core material. For example, if volume $V_1$ of the interfacial fluid provides a thickness $T_1$ of the shell encapsulating the core material, than increasing $V_1$ to $V_2$ (where $V_1 < V_2$) will increase the thickness $T_1$ to $T_2$ (where $T_1 < T_2$). For further example, changing the volume of the interfacial layer may form an encapsulated core material where the shell layer accounts for more than 50% of the volume of the encapsulated core material. Optimal ranges of thickness T may be selected by a person of skill in the art depending on the desired application or end use of the encapsulated material, by changing the thickness of the layer of interfacial fluid. In some examples, the relationship of modifying the volume V to adjust the thickness T is a non-linear relationship.

As described above, the core material may be a fluid. Any suitable fluid may be used. A skilled person will be able to select a suitable fluid depending on the particular application and any additives to be included in the core fluid, and the particular composition of the interfacial fluid and the host fluid. When the core material is a fluid, the core material may be formed as a core droplet. A droplet may be formed by any suitable means known in the art. In some examples, forming the core droplet comprises dispensing fluid from a syringe pump and needle assembly, a rotary, or an electrical actuator.

In some embodiments of the methods described herein, passing the core material through the interfacial layer comprises dropping the core material from a suitable height H from the interfacial fluid. The force of gravity will cause the dropped core material to accelerate toward the interfacial layer thereby imparting a kinetic energy to the dropped core material. Particularly, dropping the core material comprises imparting a first kinetic energy We, to the core material. If the spatial relationship between the core material and the interfacial fluid is other than vertical, then height H may be replaced with distance D or another suitable unit of measurement and another force can be used to impart kinetic energy onto the core material.

A skilled person will be able to determine a suitable height H from which to drop a core material in order to ensure a desired level of encapsulation success. In some examples, a condition for formation of an encapsulated core material for an impact height H is based on the following equation:

$$H > \frac{3(\gamma_{12} + \gamma_{23} - \gamma_1)}{\rho_1 g R_c},$$

where H is impact height, g is gravitational acceleration, Rc is radius of the core material assuming spherical geometry, $p_1$ is density of the core material, $y_{12}$ is core material/interfacial fluid interfacial tension, $y_{23}$ is interfacial fluid/host fluid interfacial tension, and $y_1$ is air/core material interfacial tension.

In some examples, the core droplet gains a kinetic energy (manifested in the form of impact Weber number $We_i$), based on the following equation:

$$We_i = \frac{\rho_1 v^2 l_c}{\gamma_1} \approx \frac{2\rho_1 g H l_c}{\gamma_1}$$

where v is velocity of the core material immediately before impacting the interfacial fluid, g is acceleration due to gravity $I_c$ is characteristic length scale typically expressed as radius of the core material assuming spherical shape, H is impact height, $y_1$ is air/core material interfacial tension, and $p_1$ is density of the core material.

As described above, in some examples, passing the core material through the interfacial fluid comprises actuating the core material from a distance D from the interfacial fluid, comprising imparting a second kinetic energy We, to the core material. The core droplet may be accelerated by any suitable means known in the art, such as but not limited to using pressure, jetting, electrostatic interactions, electrohydrodynamic actuation, or a centripetal force. For example, an adverse viscous energy barrier to encapsulation of a core material may be mitigated by suitably compensating the kinetic energy of a core droplet (e.g. by increasing impact height or by providing acceleration by other means—jetting/electrohydrodynamic actuation).

As described above, the core material may be a solid. A skilled person will be able to select a suitable solid depending on the particular application and any additives to be included in the core material, and the particular composition of the interfacial fluid and the host fluid. When the core material is a solid, the core material may be a core solid.

In some embodiments of the methods described herein, when passing the core material through the interfacial fluid, the only fluid the core material may contact is the interfacial fluid. In some embodiments of the methods described herein, forming the encapsulated core material comprises protecting the core material with the shell. In such a case, the interfacial fluid provides a barrier between the core material and the host fluid. In some examples, protecting the core material comprises preventing the core material from contacting the host fluid. This may be because the core material and the host fluid are incompatible; for example, because the core material is miscible with the host fluid, or because the core material is reactive with the host fluid, or is otherwise degradable in the host fluid.

In some embodiments of the methods and compositions described herein, one or more of the core material, the interfacial fluid, and the host fluid comprises an additive. As used herein, "additive" refers broadly to any compound, mixture of compounds, component, or mixture of components provided in any one or more of the core material, the interfacial fluid, and the host fluid. The additive may be active, reactive or inert. An additive may, for example, refer to an active additive, such as a pharmaceutical compound/active pharmaceutical ingredient (API), a reactive additive, such as a reactive chemical species, or an inert additive, such an inert excipient. These are just a few examples and should not be viewed as limiting in any way. Additives may be comprised in any one or combination of the core material, interfacial fluid, or host fluid for any suitable purpose.

The methods and compositions of the present disclosure may be used, for example, to facilitate: (i) carrying and/or delivering and/or releasing (e.g., via delayed release, controlled release, quick release, etc.) of an active ingredient to or at intended site, e.g., within the body of a subject (blood stream, gastrointestinal tract, etc.), within soil, within water, within a food or beverage product, within an agricultural product, within a cosmetic product, within a consumer product, a perfume product, etc.); and/or (ii) protecting a reactive or degradable ingredient the final, encapsulated core material from a hostile environment or hostile conditions that would otherwise degrade, dissolve, alter, or react with said compound, mixture of compounds, component, or mixture of components—for example, until said compound, mixture of compounds, component, or mixture of components can be delivered to their intended site or used for their intended purpose.

In some non-limiting examples, the additive is a pharmaceutical compound, an excipient, a food or beverage ingredient (e.g., caffeine, vitamin, nutrient, etc.), a cannabinoid (e.g., tetrahydrocannabinol, cannabidiol), an aroma compound, an enzyme, a microparticle, a nanoparticle, a surfactant, a mineral, a salt, an oil (e.g., a fish oil), a probiotic, a polymer, a water-treatment compound, or a soil-treatment compound. In some examples, the additive is disposed in a fluid phase (e.g., the core material, interfacial fluid, and host fluid are all fluids) to facilitate absorption into a subject's blood stream; or to facilitate biodegradability.

Care should be taken when deciding the concentration of the additive to ensure that the volume and/or density of the resulting mixture/suspension still meets the criteria wherein the core material can be successfully encapsulated. If necessary, parameters of the core, interfacial layer and/or host fluid may be suitably adjusted to account for the presence of additive. The kinetic energy of the core material (e.g., impact height) and/or interfacial layer volume may also be adjusted to ensure successful encapsulation.

In some embodiments of the methods and compositions described herein, the encapsulated core material comprises a condensed phase, such as a liquid, solid, or a combination thereof. When the core material is a liquid, any suitable liquid may be used. A skilled person will be able to select a suitable fluid depending on the particular application and any additives to be included in the core fluid, and the particular composition of the interfacial fluid and the host fluid. In some examples, the liquid may include, but is not limited to a liquid mixture, a solution, a suspension, a liquid polymer, or a liquid polymer mixture. For example, when the core material is a fluid, the fluid may comprise any one or a combination of: a solid suspension, an additive, a microparticle, microparticles, a nanoparticle, nanoparticles, a surfactant, food nutrients, an Omega oil, a fish oil, a probiotic, or a polymer. In some examples, the fluid a laser liquid. In some examples, the laser liquid is a mixture of silicones and polyphenol ethers. When the core material is a solid, the solid may be a polymer, a nut, or a seed.

In embodiments of the methods and compositions described herein, the interfacial fluid is a fluid. Any suitable fluid may be used. A skilled person will be able to select a suitable fluid depending on the particular application and any additives to be included in the interfacial fluid, and the particular composition of the core fluid and the host fluid. In some examples, the liquid may include, but is not limited to a liquid mixture, an oil, a solution, a suspension, a liquid polymer, a liquid polymer mixture, a liquid agar gel, a liquid gelatin, or a liquid cellulose. In some examples, the interfacial fluid is a canola oil, a silicone oil, hydroxypropylmethylcellulose, or hexanes. In some embodiments of embodiments the methods and compositions described herein, the interfacial fluid has an interfacial energy suitable for encapsulating a core material.

In embodiments of the method and compositions described herein, the host fluid is a fluid. Any suitable fluid may be used. A skilled person will be able to select a suitable fluid depending on the particular application and any additives to be included in the host fluid, and the particular composition of the core fluid and the interfacial fluid. In some examples, the liquid may include, but is not limited to a liquid mixture, a solution, a suspension, a liquid polymer, a liquid polymer mixture, a liquid agar gel, a liquid gelatin, or a liquid cellulose. In some examples, the host fluid is an aqueous liquid, such as water.

In certain embodiments of the method described herein, forming the encapsulated core material may further comprise hardening the core material or the shell. In some examples, hardening the core material or the shell comprises curing the core material to form a hardened core material, or curing the shell to form a hardened shell. In such examples, the core material may comprise for example an UV-curable epoxy resin, a biocompatible photopolymer, or a resin-based composite (e.g., a dental composite resin). In some examples, curing the shell comprises exposing the shell to ultraviolet radiation. In such examples, the shell may comprise an UV-curable epoxy resin, a biocompatible photopolymer, or a resin-based composite (e.g., a dental composite resin). In other examples, curing the shell comprises triggering a coacervate formation; or comprises exposing the shell to heat.

Certain embodiments of the methods described herein may further comprise enclosing the encapsulated core material. As used herein, enclosing refers to further encapsulating the already encapsulated core material with an additional layer of material (e.g., an enveloping layer). In some examples, enclosing the encapsulated core material comprises enclosing the encapsulated core material with a polymer sheet or an interfacial assembly of particles (e.g., the enveloping layer). Any suitable polymer sheet or an interfacial assembly of particles may be used. A skilled person will be able to select a suitable polymer sheet or an interfacial assembly of particles depending on the particular application and any additives to be included in the encapsulated core material, and the particular composition of the encapsulated core material. In examples wherein the encapsulated core material is enclosed with a polymer sheet, the polymer sheet may comprise a soft gelatin sheet, or polystyrene films.

In respect of the compositions described herein, a condition for stability of an encapsulated core material in the host fluid is based on the following equation:

$$Y_{13} > Y_{12} + Y_{23}$$

where $y_{13}$ is core material/host fluid interfacial tension, $y_{12}$ is core material/interfacial fluid interfacial tension, and $y_{23}$ is interfacial fluid/host fluid interfacial tension.

In some embodiments the compositions described herein, the shell is a hardened shell. In some examples, the hardened shell comprises a cross-linked interfacial fluid. In such examples, the shell may comprise a cross-linked epoxy resin, biocompatible photopolymer, or resin-based composite (e.g., a dental composite resin). In other examples, the hardened shell comprises a coacervate formation formed from the interfacial fluid.

In certain embodiments of the method compositions described herein may further comprise an enveloping layer enclosing the encapsulated core material, where enclosing refers to further encapsulating the already encapsulated core material with the enveloping layer. The enveloping layer may comprise a polymer sheet or an interfacial assembly of particles. Any suitable polymer sheet or an interfacial assembly of particles may be used. A skilled person will be able to select a suitable polymer sheet or an interfacial assembly of particles depending on the particular application and any additives to be included in the encapsulated core material, and the particular composition of the encapsulated core material. In examples wherein the encapsulated core material is enclosed with a polymer sheet, the polymer sheet may comprise a soft gelatin sheet, or polystyrene films.

In some embodiments of the compositions as described herein, the shell may comprise at least a first and a second interfacial fluid, and the core material is encapsulated with a first shell formed from the first interfacial fluid, and the first shell is encapsulated with a second shell formed from the second interfacial fluid.

In another aspect of the disclosure, there is provided an encapsulated core material prepared by any one of the methods described herein. In some examples, said encapsulated core material is present (e.g. dispersed or suspended) in a host fluid.

In some embodiments of the methods, compositions, and encapsulated core materials as described herein, the encapsulated core material does not comprise emulsions, such as double emulsions or multiple emulsions. In some embodiments of the methods, compositions, and encapsulated core materials as described herein, the encapsulated core material is not prepared via a jet breakup mechanism; and/or, encapsulation of the core material does not occur via a jet breakup mechanism. In some embodiments of the methods, compositions, and encapsulated core materials as described herein, the encapsulated core material is not prepared via a microfluidic device; and/or, encapsulation of the core material does not involve a microfluidic device.

In another aspect, there is provided a use of the encapsulated core material made by the methods described herein, or the compositions described herein. In some embodiments, the compositions are for use carrying, delivering and/or releasing an active ingredient. In some embodiments, the active ingredient is a food or drug ingredient, such as a pharmaceutical compound. Further described herein is a use of the encapsulated core material made by the methods described herein, or the compositions described herein for sustained or delayed release of an active ingredient, such as a pharmaceutical compound. In some examples, there the encapsulated core material is used for controlled release of an additive, such as a pharmaceutical compound, or for quick release of a pharmaceutical compound. In another aspect, there is provided a pharmaceutical composition comprising a liquid-encapsulated core material comprising at least one active pharmaceutical ingredient; and a pharmaceutically-acceptable excipient, carrier or diluent. In some embodiments, the core material is a carrier or diluent for the pharmaceutical ingredient. In some embodiments, the host fluid is the carrier for the liquid-encapsulated core material comprising the at least one active pharmaceutical ingredient. In accordance with embodiments of the disclosure, the pharmaceutical composition may be formulated for administration to a subject by any suitable means, for example, oral, parenteral, or topical administration. Parenteral administration bypasses the GI tract and includes, for example, intravenous, intramuscular, intrathecal and subcutaneous administration among others. The composition may be prepared in any suitable dosage form, such a solution, suspension, cream, gel, or ointment, among others.

Also described herein is a use of the encapsulated core material made by the methods described herein, or the compositions described herein in a cosmetic product. Further described herein is a use of the encapsulated core material made by the methods described herein, or the compositions described herein for delayed release of an additive in or from a cosmetic product. In some examples, the encapsulated core material is used for controlled release of an additive in or from a cosmetic product, or for quick release of an additive in or from a cosmetic product. In some examples, the additive may comprise any one or combination of a time-release moisturizer, a time-release wrinkle smoother, a time-release recovery cream, or a time-release acne cleanser (with controlled release of salicylic acid).

In some embodiments as described herein is a use of the encapsulated core material made by the methods described herein, or the compositions described herein, in an emulsion or suspension.

Also described herein is a use of the encapsulated core material made by the methods described herein, or the compositions described herein for encapsulating a food product. Further described herein is a use of the encapsulated core material made by the methods described herein, or the compositions described herein in a food product. In some examples, the encapsulated core material is used for delayed release of an additive from a food product; or for controlled release of an additive from a food product; or for quick release of an additive from a food product. In some examples, the additive comprises a vitamin, an enzyme, a nutraceutical, an oil (e.g., a fish oil), an omega fatty acid (e.g., omega 3 fatty acid), caffeine, a cannabinoid (e.g., tetrahydrocannabinol, cannabidiol), or a probiotic. In some examples, the food product is a beverage, a nutraceutical, a confectionary, an oil (e.g., a fish oil), an omega fatty acid (e.g., omega 3 fatty acid), a seed, a nut, or a probiotic. For example, seeds or nuts may be a core material of an encapsulated core material, wherein being encapsulated by a shell of interfacial fluid protects the seed or nut from oxidation.

Described herein is a kit comprising a host fluid, an interfacial fluid, and a core, and instructions for use thereof. The kit may further comprise an additive and instructions for adding the additive to any one of the core material, the interfacial fluid, or the host fluid. Further described herein is a kit comprising a host fluid, a encapsulated core material in the host fluid, and instructions for use thereof. The kit may further comprise an additive and instructions for adding the additive to any one of the encapsulated core material, or the host fluid. In some examples, the additive is a pharmaceutical compound, a food or beverage ingredient (e.g., caffeine, vitamin, nutrient, etc.), an excipient, a cannabinoid (e.g., tetrahydrocannabinol, cannabidiol), an aroma compound, an enzyme, a microparticle, a nanoparticle, a surfactant, a mineral, an oil (e.g., a fish oil), a probiotic, a polymer, a water-treatment compound, or a soil-treatment compound. In some examples, the additive is disposed in a fluid phase (e.g., the core material, interfacial fluid, and host fluid are all fluids) to facilitate absorption into a subject's blood stream; or to facilitate biodegradability.

Definitions

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

The term "subject", as used herein, refers to an animal, and can include, for example, domesticated animals, such as cats, dogs, etc., livestock (e.g., cattle, horses, pigs, sheep, goats, etc.), laboratory animals (e.g., mouse, rabbit, rat, guinea pig, etc.), mammals, non-human mammals, primates, non-human primates, rodents, birds, reptiles, amphibians, fish, and any other animal. In a specific example, the subject is a human.

To gain a better understanding of the invention described herein, the following examples are set forth. It should be understood that these examples are for illustrative purposes only. Therefore, they should not limit the scope of this invention in anyway. The inventors do not wish to be bound by any scientific or mathematical theories presented in the specification or examples.

EXAMPLES

Example 1—Encapsulation with an Interfacial Liquid Layer: Robust and Efficient Liquid-Liquid Wrapping Encapsulation enables isolation/protection and timely release of a core additive. Herein described is an efficient, robust method of encapsulation where a core droplet is stably wrapped by an interfacial liquid film (shell) upon being impinged on it from a vertical separation. A complex yet ultra-fast interplay between gravitational and interfacial energies governs this process. The volume of the interfacial layer and the kinetic energy of the core droplet before impact are identified to be the key control variables and their influence is presented in a regime map demarcating successful and unsuccessful encapsulation (e.g., see FIG. 3). The practical potential of the method is established by demonstrating its ability in protecting a vulnerable (miscible) core from an aggressive surrounding. With its robustness, scalability, wide operational spectrum, minimal restrictions on core-shell selection and potential ability in enhancing dosage efficiency and biocompatibility owing to a liquid wrapping layer, the proposed method suggests new pathways to stable liquid-based encapsulation.

More particularly, herein described is a method to achieve encapsulation in an ultra-fast, robust yet efficient manner utilizing a fundamental characteristic of liquid, i.e., minimization of its interfacial energy. The herein described method is built upon the fundamentals of the impact driven water entry problem. A wide volume of scientific endeavour is dedicated to understanding the dynamics of impact of solid objects as well as liquid droplets on a liquid pool. The herein described method introduces an intermediate layer in the traversal path of the droplet and exploits the resulting complex interfacial dynamics that leads to formation of a stable and consistent liquid based wrapping layer.

Materials

The method involves three liquids, namely the core droplet (liquid 1, L1; core material), the interfacial layer forming the shell (liquid 2, L2; interfacial fluid) and the liquid bath (liquid 3, L3; host fluid) that houses the encapsulated drop (encapsulated cored material) after it settles down. If not otherwise mentioned, a particular class of laser liquid—a mixture of silicones and polyphenol ethers, with a water solubility of <0.1% (Product Code: 57B63, Cargille Laboratories Inc., Cedar Grove, NJ, USA) was used to form the core droplet. Relevant material properties were as follows: density $p_1$=1900 kg/m 3, dynamic viscosity $\mu_1$=1024 mPa-s, liquid-air surface tension $y_1$=50 mN/m, liquid-canola oil interfacial tension $y_{12}$=2.22 mN/m and liquid-water interfacial tension $y_{13}$=39.4 mN/m. The interfacial layer that ultimately wraps the core droplet was composed of canola oil (manufactured and marketed under the brand name of Clic International Inc., Ottawa, Canada), with density $p_2$=913 kg/m$^3$, dynamic viscosity $H_2$=63.5 mPa-s, liquid-air surface tension $y_2$=31.3 mN/m and liquid-water interfacial tension, $y_{23}$=18.01 mN/m. The host liquid was chosen to be deionized water (purified by Milli-Q, MilliPoreSigma, Ontario, Canada) with density $p_3$=1000 kg/m$^3$, dynamic viscosity $p_3$=1 mPa-s and liquid-air surface tension $y_3$=72 mN/m.

The experiments were conducted in a distortion-free glass cuvette (Product Code: SC-02, Kruss GmbH, Hamburg, Germany) of inner dimension 36 mm×36 mm×30 mm with 2.5 mm wall thickness. The solid substrate used for studying the wetting signature was poly(methyl methacrylate) (PMMA). PMMA sheets of dimensions 150 mm×150 mm with 1 mm thickness (Plaskolite Inc., Columbus, Ohio, United States) were diced into 25 mm×25 mm square pieces for using as substrate material. For liquid dispensing purposes, polished and passivated stainless-steel needle tips with gauge 14 and inner diameter of 0.060" (Part No. 7018035, Nordson EFD, East Province, RI, USA) were used.

To render the interfacial layer optically opaque and ensure confirmatory visual differentiation, the interfacial oil layer was mixed with a partially oil soluble particle-based dye (Product Name: OrcoSolve Quinoline, Organic Dyes and Pigments, Rhode Island, RI, USA). To ensure homogeneity, the prepared suspension was thoroughly mixed using a vortex mixer (Product catalog No. 02-215-422, Fisherbrand Pulsing Vortex Mixer, Fisher Scientific, Ottawa, Ontario, Canada) at 2700 rpm for 1 minute before conducting the experiments.

A commercial oil soluble fluorescent dye (TP 3400, Tracer Product) was mixed with the interfacial liquid L2 in 0.12% volume/volume ratio to aid visual differentiation between the encapsulated and unencapsulated drop. The surface tension values of the interfacial oil solution were confirmed to remain unaltered due to the addition of the dye.

Method

For the herein described method, first, the cuvette was partially filled with a predetermined quantity of the host liquid (here with 24 ml of water). However, minor variations in the volume of the host liquid (±2 ml) was seen to cause no noticeable effect on the process dynamics. A syringe pump and stainless-steel needle (disposable) assembly were used thereafter to dispense the interfacial liquid concentrically on the top of the host liquid-air interface. A slow and controlled liquid dispensation was used to prevent disruption of the interfacial layer due to sudden influx of the discharged liquid. The core droplet was generated thereafter at a slow and steady flow rate from a height H from the interface (with H being the vertical separation between the droplet and the canola-air interface) using the same dispensing system. FIG. 1A depicts a step-wise schematic representation of the herein described method.

For a proof of concept, external actuation was not induced to force drop detachment from the needle. Consequently, the resulting droplet volume was determined by an interplay between the surface energy of the needle tip and effect of gravity and therefore remained invariant as long as the same class of needle tip and liquid combination was used. During the generation process, the core drop grew till a volume when the surface tension forces at the needle tip could no longer sustain its weight and it detached from the needle tip thereafter due to gravity. This volume was determined by the outer diameter of the needle, the liquid-air surface tension, and the effect of gravity. In the herein described experiments, the average nominal volume of the core Laser oil drop was found to be 15.5 μL with a standard deviation of 0.8 μL. Assuming spherical geometry, this average volume corresponded to a radius of 1.54 mm, which was below the capillary length-scale. Precautions were taken while choosing the needle diameter, so that the size of the resulting core drop size was below capillary length scale, thereby eliminating unpredictable influences of gravitational forces on the droplet dynamics. However, it was found that there was no qualitative difference in the encapsulation process even if the drop radius was higher than the capillary length-scale. Droplets with a radius larger than the capillary length scale were successfully encapsulated in a similar manner implying that there was no fundamental restriction on the upper limit of usable droplet volume for the herein described method.

To eliminate unwanted movement of interfacial layer and consequent loss of concentricity in liquid dispensing during the experiments, usage of a stable, horizontal, vibration free platform was used. Any movement of the experimental set up was minimized during the process, if not completely avoided. The experiments reported herein were performed on a vibration isolating optical table.

Results and Discussion

Experimental Visualization of a Typical Encapsulation Process

Figure 10:
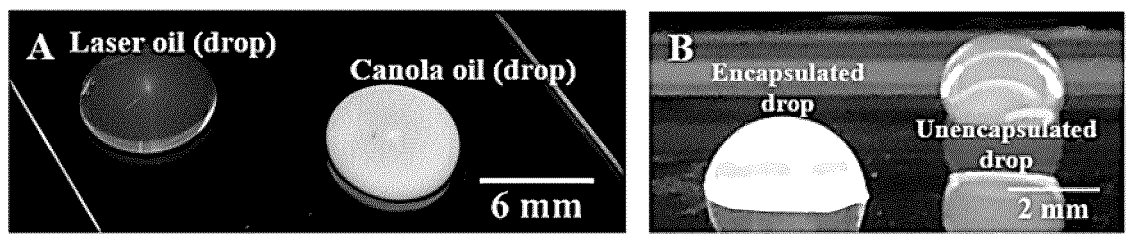
FIG. 10 depicts a fluorescent characterization of the encapsulation layer: Fluorescent signature of (A) laser oil and dyed canola oil drop, (B) encapsulated and unencapsulated drops inside host water bath upon being excited with 365 nm ultraviolet source.

A typical encapsulation process is illustrated in FIG. 10-1E for interfacial film volume $V_{film}$=350 µL and impact height H=6.5 cm. Upon detachment from the dispensing needle, the core droplet traversed through air before it comes in contact with the interfacial layer of L2. At the point of first contact with this interfacial layer, the droplet possessed a kinetic energy equal to the weight of the droplet multiplied by the impact height H (assuming negligible viscous dissipation in air). Upon contact the droplet attempted to penetrate through this intermediate layer. During its time of flight through interfacial layer, the droplet undergoes a complex non-trivial interaction where its kinetic energy facilitates the formation of a secondary wrapping layer of the interfacial liquid. Initially the droplet tried to drag the interface downward along it but after a while the interface attempted to retract back to its original position. If the droplet had sufficient kinetic energy, this competition lead to neck formation and subsequent separation of the droplet from the interface (as illustrated in the third time stamp corresponding to T=24.22 ms in FIG. 10).

Put another way, upon contact with the interfacial layer, the core drop attempts to penetrate through the intermediate layer. There are three competing effects that govern the penetration process. The core drop drags the L2 layer downward due to its momentum, which deforms the interface and increases its surface area. However, interfacial forces acting on the deformed L3-L2 and L2-L1 interfaces attempt to restore the interface back to its original position to minimize the interfacial energy. The viscous resistance of the interfacial layer also opposes the downward motion of the drop by dissipating its momentum. This competition leads to neck formation (time stamp T=24.22 ms in FIG. 10). If the drop has sufficient momentum to overcome the barrier imposed by both the interfacial forces and the viscous resistance, then it can penetrate through the interfacial L2 layer, as is the case illustrated in FIG. 10 (see the time stamp T=42.97 ms).

In the process the core drop detached a part of the film from the interfacial layer. This detached layer formed a thin enclosure (the encapsulating shell) around the core droplet. To elaborate this non-trivial interface evolution further, two different stages of encapsulation process has been zoomed in in FIGS. 1D and 1E. FIG. 1D demonstrates the necking process that lead to ultimate separation of droplet from interface, while FIG. 1E illustrates the enclosure formation around the core drop. In both the cases the outlines of the core drop and shell layer were distinctively visible and are highlighted for clarity. Although complex, this process was ultrafast with a typical successful encapsulation requiring only tens of milliseconds to complete.

Figure 7:
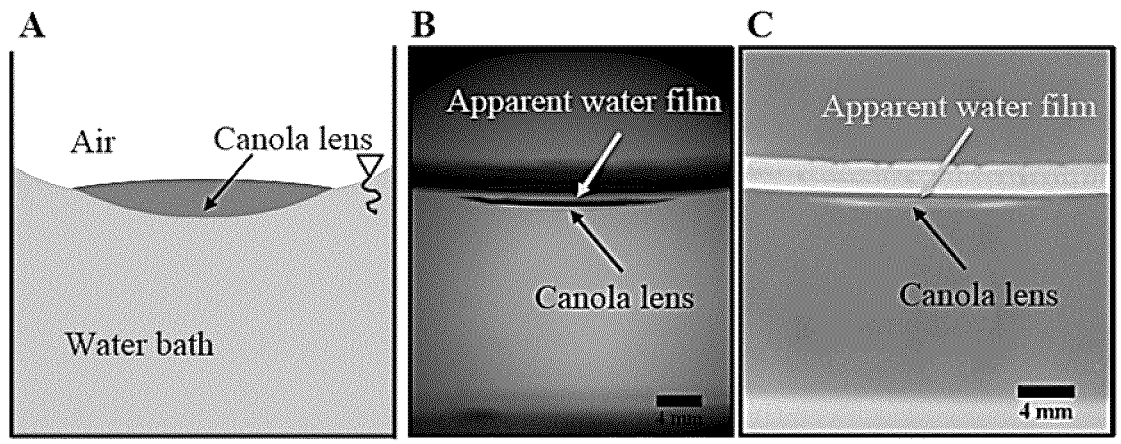
FIG. 7 depicts shape of interfacial layer— (A) Schematic representation (not to scale) of the canola lens floating on top of a water bath, (B) grayscale experimental image of the interfacial layer captured with a high-speed camera after 220 μL of canola oil dispensed on top of a water bath (4 mm scale bar) (C) image of the interfacial layer in same experimental set up captured using a digital SLR camera from a plane perpendicular to that of the high-speed camera.

Another consideration here was the equilibrium shape of the interfacial layer L2 that depended on the values of surface and interfacial tensions (manifested in the spreading parameter $S=y_3-y_{23}-y_2$) and the dispensed volume. With S being positive, canola drops were seen to spread on top of the water-air interface as soon as they came in contact with water and ultimately formed a floating oil lens with one side in contact with water while the other side was exposed to air. Although from some experimental images, it might appear that there existed an intermediate water film preventing direct contact of the canola lens with air, the possibility of formation of such a pseudo-total wetting state has been refuted both theoretically and experimentally (see section S1 and FIG. 7 in Example 2).

The interfacial layer had the maximum film thickness at the centre of the lens and the geometric profile of the lens was symmetric about a vertical axis passing through this centre. It is desirable to map the output parameters (resulting shell thickness, encapsulated volume etc.) in terms of thickness of the interfacial film instead of its volume. However, in the herein described method, the film volume was the parameter that could be precisely controlled while the maximum film thickness was a complex function of the dispensed volume as well as the interfacial energies. Therefore for quantification of the extent of encapsulation, the volume of the interfacial film was chosen to be the control parameter instead of its thickness.

Also the non-uniform interfacial layer thickness and the intrinsic fluidity of the interfacial layer made this process considerably different from methods involving solid polymer sheets, where an elastic sheet of a known uniform thickness is wrapped in its entirety around a core drop rendering the determination of resulting shell thickness (equal to initial polymeric sheet thickness) and the core-shell interfacial area trivial. On the contrary, for the herein described method, successful encapsulation was preceded by detachment of only a part of the interfacial layer via necking, which ultimately formed the shell. The extent of this detachment was determined by a complex interfacial interplay between gravity, interfacial energies, viscosity of the film layer and the kinetic energy of the core and was not straightforward to estimate. Even uniformity of the encapsulation structure could not be guaranteed owing to the fluidity of the encapsulating phase. Therefore, despite multiple added advantages e.g., simplicity, robustness and ability to enhance bioavailability, a complete theoretical prediction of such a liquid wrapping process was found to be much complex and intricate in comparison to its solid/semi-solid counterparts.

Dye Assisted Visualization of Encapsulation Process

Although visible, the distinctive identification of the core-shell structure in FIG. 1C-1E still remained subjective in nature as both the core drop and the shell layer were optically translucent. To facilitate objective visualization, an encapsulation experiment was carried out for an impact height of 8 cm in the presence of an interfacial film of volume 150 µL consisting of an optically opaque, homogeneously dyed suspension. The suspension was prepared by thoroughly mixing 2.5 gm of a yellow particle-based dye with 100 mL of canola oil. The surface tension values of the prepared suspension were measured using pendant drop tensiometry and found to remain invariant upon addition of dye (see Table 1 in Example 2). The calculated value of surface tension of the dyed suspension was 32.36 mN/m, while the undyed canola oil had a surface tension of 31.3 mN/m. However, it was noted that upon addition of dye, the density and viscosity of the interfacial liquid change in comparison to that of undyed canola oil. The density increases to 926 kg/m$^3$, which was still less than of the host liquid, because of which the interfacial layer remained stably suspended on the host water bath underneath. However, due to addition of the dye, the average viscosity increases to 71.82 mPa-s in comparison to 63 mPa-s in undyed canola oil. Care was taken while deciding the concentration of the dye to ensure that the density of the resulting suspension was lower than water and the interfacial film can float stably on the water-air interface. However the viscosity of the layer increased significantly, mandating necessary modification in the interfacial film volume and/or the impact height to ensure successful encapsulation.

Figure 2:
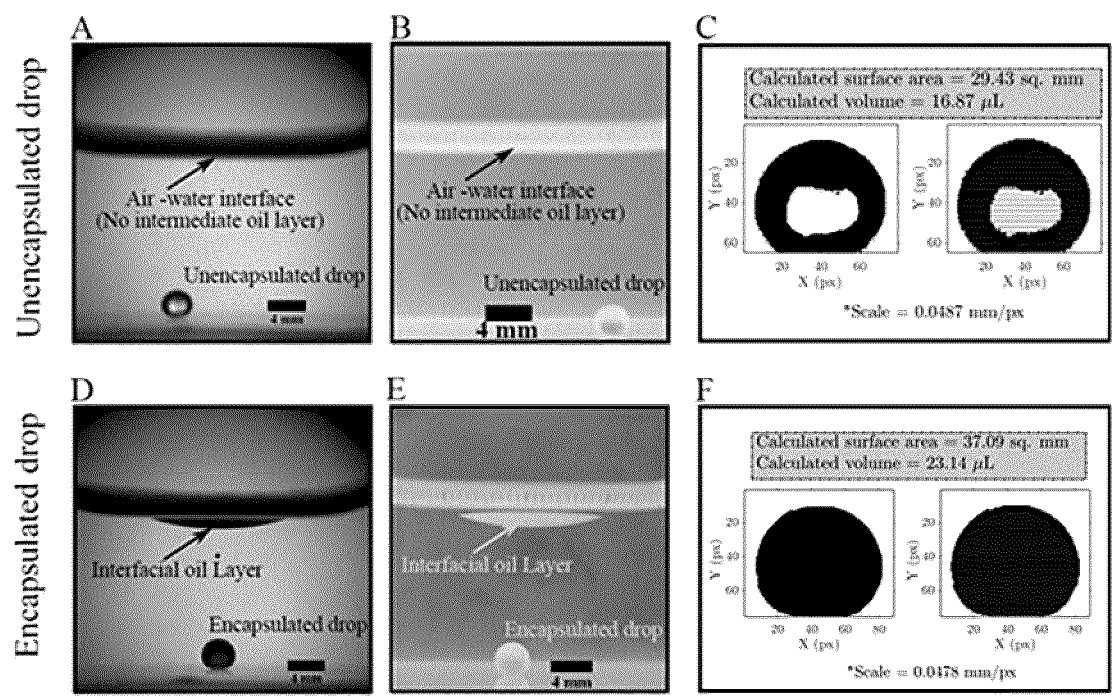
FIG. 2 depicts dye assisted visualization of encapsulation process: (A, D) represent grayscale images of settled unencapsulated and encapsulated drops respectively captured using high speed camera. (B, E) provides another visualization of the unencapsulated and encapsulated drops respectively captured using a digital SLR camera from a plane perpendicular to that of high-speed camera. (C, F) represents the extracted drop shape (using image processing) and volume calculation using vertical stack of cylinders with varying radius at pixel level resolution for the unencapsulated and encapsulated drops respectively. For the encapsulation experiment reported herein, the interfacial film volume (consisting of dyed canola oil suspension), $V_{film}$ is 150 µL and the impact height, H is 8 cm.
Figure 5:
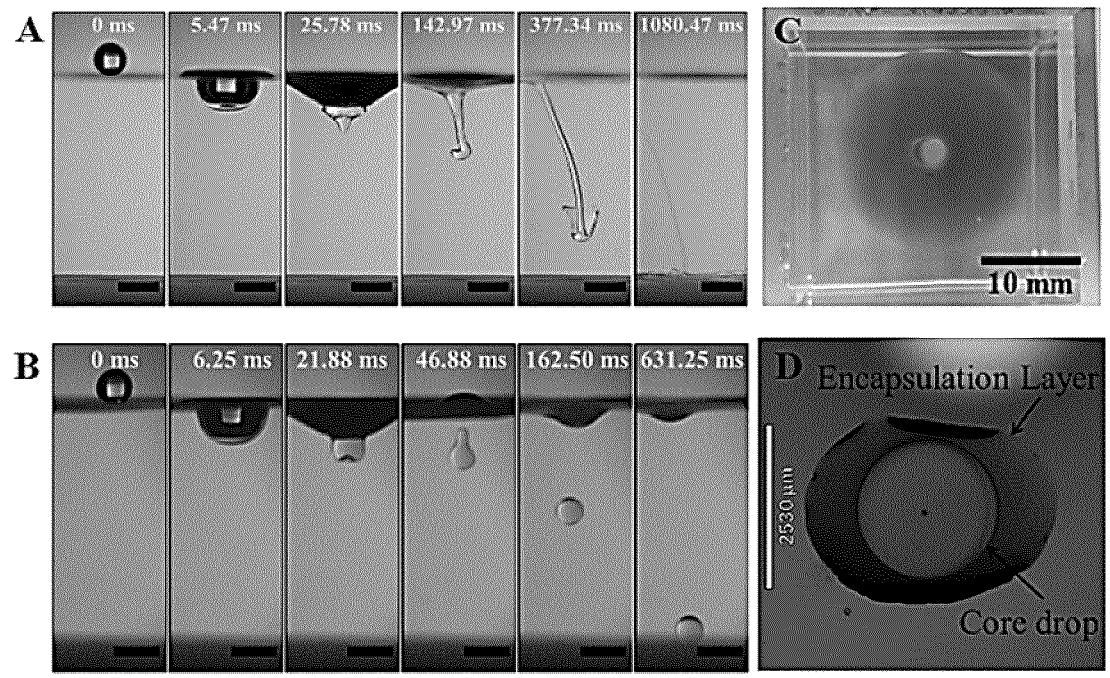
FIG. 5 depicts evaluation of potential of the herein described method in safeguarding the core drop from an aggressive (miscible) environment. (A) Time series illustrating the water entry of an ethylene glycol drop. Due to its miscibility in water, the drop gets dissolved in the surrounding medium upon its entrance. (B) Time series demonstrating the water entry of another ethylene glycol drop of same volume—this time the droplet passed through an interfacial layer of canola oil (V$_{film}$=220 μL) before it entered the water bath. (C) Post-encapsulation top-view of the interfacial canola layer. (D) Bottom view of the encapsulated drop captured via bright-field optical microscopy. If not explicitly mentioned otherwise, the scale bar represents 4 mm wherever applicable.

Successful encapsulation yielded an encapsulated drop with a distinctively visible all-around yellow wrapping layer. While the unencapsulated drop remained translucent, the encapsulated drop turned optically opaque, as can be seen from the grayscale image captured with a high-speed camera as well as the image captured with a digital SLR camera (see FIG. 2). Assuming axis-symmetric drop shape, the volumes of both the encapsulated as well as unencapsulated drops were calculated using the image processing protocol described in section S3 and FIG. 8, Example 2. The encapsulated drop registered 37% more volume in comparison to its unencapsulated counterpart. This volume increment was considered to only be attributed to the formation of an encapsulating layer. The aforementioned differences between the two drops served as additional evidence of encapsulation. Contextually, it was noted that the post encapsulation volume increment does not require usage of dye in interfacial layer. Even in the absence of any dye, the encapsulated drop registered a higher volume than its unencapsulated counterpart (as can be confirmed from the side-by-side visual comparison of drop size in FIG. 1C as well as from the reported values of encapsulated drop volume in FIG. 5).

Figure 9:
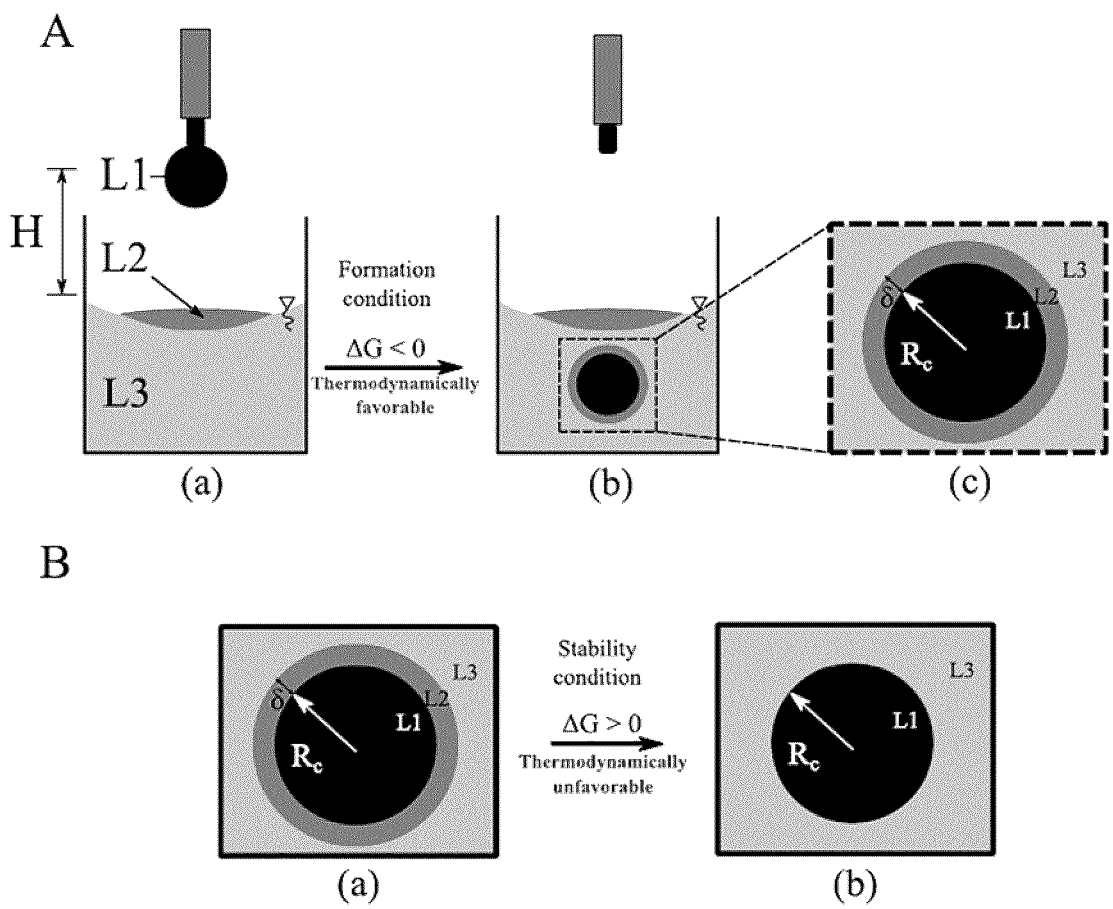
FIG. 9 depicts a schematic illustration (not to scale) of the criteria for the formation and stability of the encapsulated state: (A) Formation of an encapsulated drop is thermodynamically feasible when the Gibbs free energy change during the transition from state (a) to (b) is negative. A zoomed in view of the encapsulated drop is provided in (c) with relevant geometric parameters used in the calculation of free energy change. (B) The encapsulated drop remains stable upon formation if the transition from state (a) to state (b) is thermodynamically unfavorable i.e. has an associated positive free energy change.

Theoretical Criteria Governing the Formation and Stability of Encapsulation: An Equilibrium Thermodynamics Perspective For the herein described encapsulation process to be successful, two main criteria needed to be fulfilled. As the interfacial layer (L2) maintains direct contact with the host liquid (L3), L2 and L3 need to be physicochemically compatible (i.e., mutually unreactive, immiscible). Additionally, as the interfacial layer was required to float on top of the host liquid and the motion of the core droplet inside the liquid pool was assisted by gravity, a favorable density regime for the herein described method required the core drop (L1) to have the highest density among three participating liquids, followed by the host liquid (L3) and the interfacial layer (L2) respectively ($p_1 > p_3 > p_2$). It was noted that the condition $p_3 > p_2$ was a sufficient condition for the stability of the interfacial layer, not a necessary one as an interfacial layer consisting of a small amount of a heavier liquid could also float on top of lighter liquid bath given it is placed gently and from close vicinity. Additionally, thermodynamic favorability of this encapsulation layer formation required the Gibbs free energy change in the process to be less than zero, which yielded the following necessary criterion for successful encapsulation for an impact height H:

$$H > \frac{3(\gamma_{12} + \gamma_{23} - \gamma_1)}{\rho_1 g R_c}, \quad (1)$$

where g is gravitational acceleration and Rc is the radius of the core droplet assuming spherical geometry. However, H being a positive variable, if $y_{12}+y_{23}-y_1<0$, Eq.(1) was automatically satisfied making $y_{12}+y_{23}-y_1<0$ a sufficient condition for successful encapsulation. Additionally, for the encapsulated drops to be stable upon formation, the interfacial energies of the participating liquids needed to satisfy the following criterion: $y_{12}+y_{23}<y_{13}$. See section S4 and FIG. 9 in Example 2 on the underlying assumptions and the derivation of both the criteria. Water, canola oil and laser oil triad satisfied both of these theoretical criteria which explained the feasibility of formation and stability of the encapsulating layer of canola oil around laser oil core drop when hosted in a water bath.

Role of Impact Weber Number and Interfacial Film Volume on Successful Encapsulation: Deviation from Idealized Theoretical Estimate It was recognized that merely satisfying the condition: $y_{12}+y_{23}<y_1$ did not guarantee successful encapsulation as the equilibrium thermodynamic analysis assumes the encapsulation process to be reversible and consequently does not take into account the viscous interaction between the core droplet and the interfacial layer, which is a crucial contributor in the interfacial dynamics (see section S4 in Example 2 for detailed theoretical explanation). During its traversal through air before its impact with the interfacial layer, the core droplet gains a kinetic energy (manifested in the form of impact Weber number $We_i$, calculated as $$We_i = \frac{\rho_1 v^2 l_c}{\gamma_1} \approx \frac{2\rho_1 g H l_c}{\gamma_1}$$

where v is velocity of the core drop immediately before its impact with the interfacial layer, g is acceleration due to gravity and $l_c$ is the characteristic length scale typically expressed as the radius of the drop (assuming spherical shape) proportional to the impact height H that aids penetration and consequent encapsulation process. The droplet needs to possess sufficient kinetic energy at the time of its impact with the interfacial layer to overcome the viscous barrier imposed by interfacial film layer. Any increase in the thickness of this layer corresponds to an enhanced resistance in the penetration process, forcing a transition towards the thermodynamically unfavourable regime. Therefore, to ensure the success of the process even at an increased layer thickness, a corresponding compensation needs to be arranged in the form of an enhancement in the impact kinetic energy. As can be seen from FIG. 3A, 3B, even though the droplets had the same kinetic energy at the time of impact (same $We_i$), in the first case the droplet encountered a lower interfacial volume leading to successful encapsulation while in the later case the drop experienced an increased layer thickness and consequently failed to separate from the interface.

Figure 14:
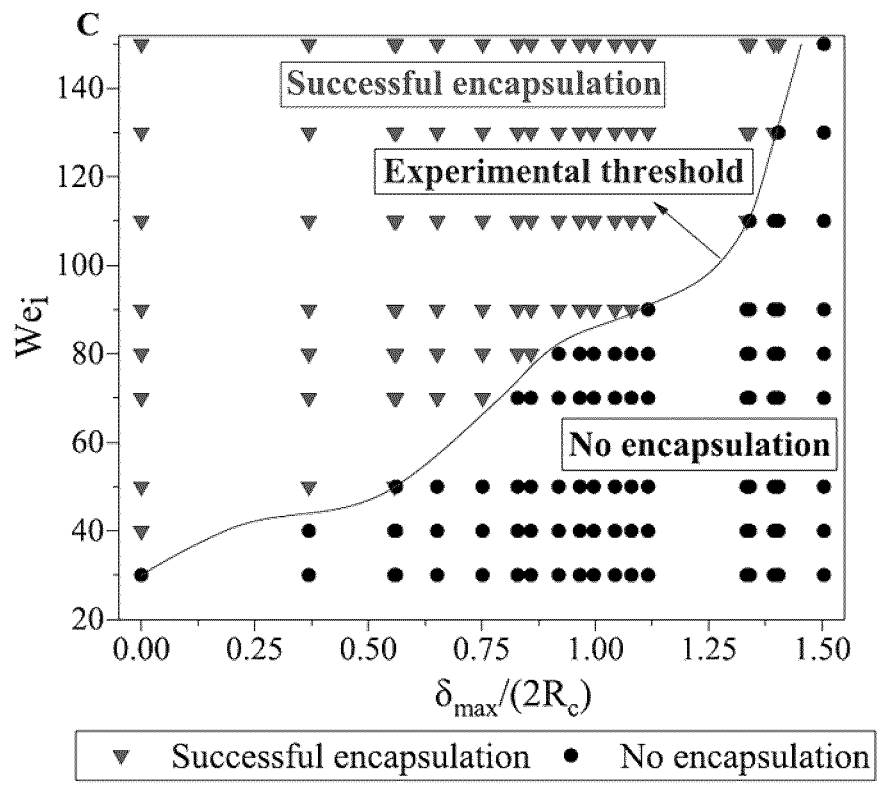
FIG. 14 depicts (C) a regime map demonstrating dependence of the success of encapsulation process on We, and δ$_{max}$/(2Rc). The experimental threshold for the same is illustrated by the zone boundary separating the two regimes—successful encapsulation and no encapsulation. The scale bar represents 4 mm wherever applicable throughout the figure.

In FIG. 3C, a non-dimensional regime for successful encapsulation is identified in terms of the impact Weber number ($We_i$) and interfacial film volume non-dimensionalized with respect to the volume of the core drop ($V_{film}/V_{core}$). For lower interfacial film volume, successful encapsulation is achieved even at low Weber number while a higher film volume (and therefore an increased intermediate film thickness) mandates a higher impact Weber number for success in encapsulation owing to the augmented kinetic energy requirement to overcome the viscous energy barrier. In FIG. 14, a non-dimensional experimental regime for successful encapsulation is identified in terms of the impact Weber number ($We_i$) and interfacial film thickness non-dimensionalized with respect to the diameter of the core drop ($\delta_{max}/(2Rc)$). For lower $\delta_{max}$, successful encapsulation is achieved even at low Weber number while a higher $\delta_{max}$ (and therefore an increased intermediate film thickness) requires a higher impact Weber number for success in encapsulation, owing to the augmented kinetic energy requirement to overcome the viscous energy barrier.

Confirmation of Stability and Integrity of Encapsulation & the Dependence on Interfacial Film Volume In the encapsulated drops, the shell layer being lighter than the core and intrinsically mobile (liquid phase), it exhibited a tendency to move up (without getting detached from the core) and form a crown like structure. Due to this accumulation at the apex of the drop, the shell layer lost its uniformity in thickness. It was more pronounced particularly while dealing with large interfacial film volumes, as can be seen in FIG. 3A. Consequently confirmation of the integrity and all-around existence of the shell layer was considered necessary, as otherwise existence of the encapsulating layer at the bottom part of the drop could be questioned. The wetting signature of the concerned entities was analyzed to validate this aspect of integrity of encapsulation. Numerous studies in literature both in experimental as well as theoretical fronts, have studied the evolution of wetting signature as a unique identifier of solid-liquid surface interaction, both for ambient as well as under-liquid applications.

Figure 4A:
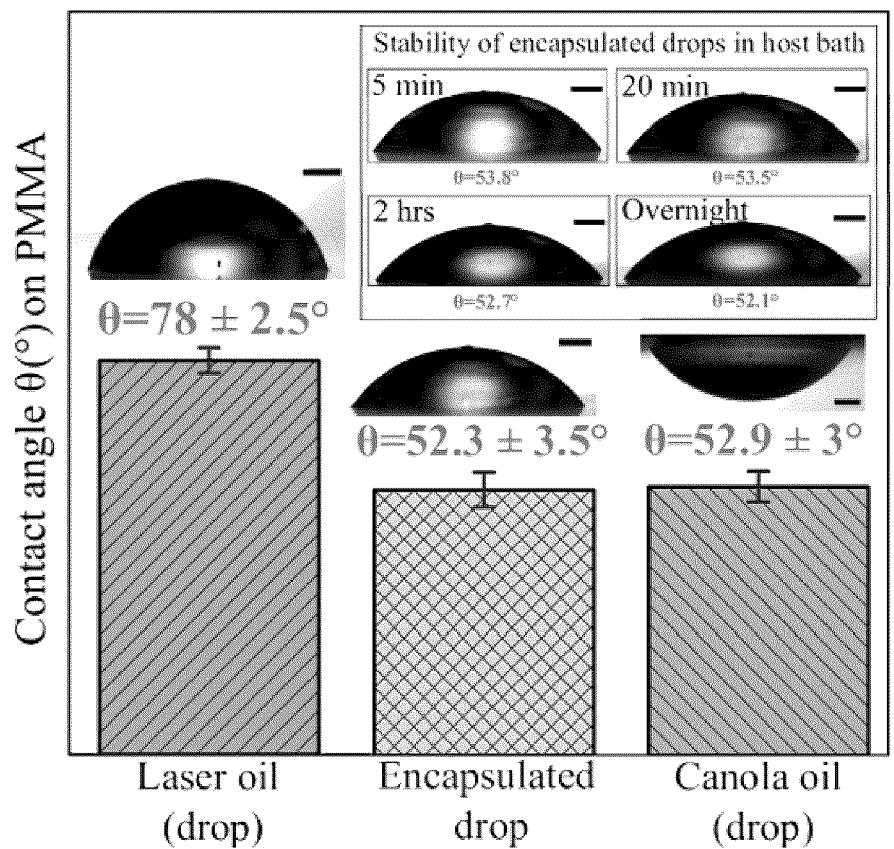
FIG. 4 depicts stability and integrity of encapsulation and dependence of extent of encapsulation on interfacial film volume. (A) Wetting signature of core liquid (laser oil), shell liquid (canola oil) and the encapsulated drop on PMMA substrate. The inset provides equilibrium shapes and the corresponding contact angle values of the encapsulated drop after it was allowed to settle for 5 minutes, 20 minutes, 2 hours and overnight. (B) a visual comparison between the fluorescent signatures of the encapsulated and unencapsulated drop at an excitation wavelength of 365 nm. An oil soluble fluorescent dye was mixed with the interfacial liquid to aid visualization (see section S5 and FIG. 10 in the Example 2 for further details). The difference in contact angle between two drops also was readily identifiable. (C) Quantification of the extent of encapsulation with change in the volume of interfacial layer: Dependence of encapsulated/settled drop volume, theoretically estimated encapsulated film thickness, encapsulation/penetration time and contact angle (on PMMA) on interfacial film volume. The calculated shell thickness is plotted in a semi-log scale in the right Y axis, while the rest are represented in linear scale on the left Y axis. The inset demonstrates the variation in core drop volume and the corresponding encapsulated shell volume with interfacial film volume. (D) Equilibrium outlines of encapsulated drops for different interfacial film volume. The scale bar represents 0.75 mm wherever applicable throughout the figure.
Figure 4B:
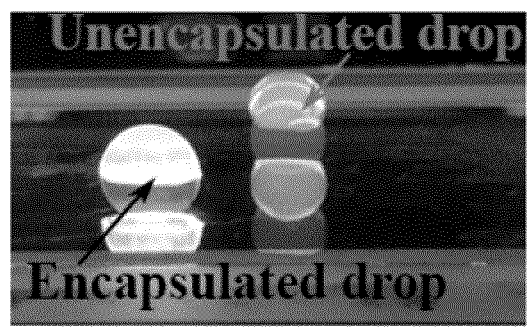
Figure 11:
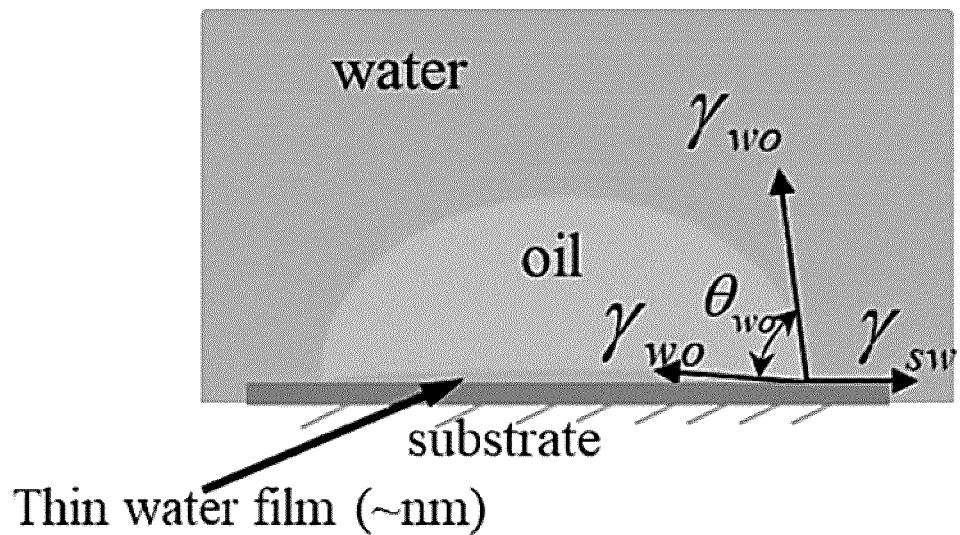
FIG. 11 depicts a schematic representation (not to scale) of the wetting situation assuming formation of a hypothesized thin water film (adopted from (6)). y$_{ij}$ refers to the interfacial tension between phase i and j, where (i,j) ∈{s,w, o}. Here s represents the solid substrate and w denotes the surrounding water medium while o stands for the oil droplet.

For this purpose, separate under water contact angle measurements of laser oil (core liquid), canola oil (interfacial liquid) and encapsulated drop were carried out on a Poly(methyl methacrylate) (PMMA) substrate. Unlike optical glass and quartz substrates, the distinctive wetting behavior of PMMA towards the chosen core and shell liquids made it an excellent substrate for studying the alteration in wetting signature due to encapsulation. Experimental results revealed (FIG. 4A) that the wetting signature of the laser oil drop in water (with a measured contact angle, $\Theta=78\pm2.5°$) differed significantly from that of a canola oil drop in water ($\Theta=52.9\pm3°$). However, the wetting characteristic of the encapsulated drop (i.e., laser oil core drop enclosed in a thin layer of canola oil) exhibited a contact angle of $\Theta=52.3\pm3.5°$, resembling the wetting signature of pure canola oil drop in water medium ($\Theta=52.9\pm3°$). Recently hypothesized was the possible formation of a sub-nanometer scale thin film between the droplet and a given substrate such as glass, when kept in a surrounding viscous medium. This can significantly influence the wetting behavior in under-liquid operation. However, for the herein described method, the prospect of such a thin film formation between PMMA substrate and the encapsulated drop was not possible theoretically (see section S6 and FIG. 11 in Example 2). Therefore, the striking similarity in wetting signature served as evidence of the integrity and all-around existence of canola oil encapsulation layer around the laser oil core droplet. Additionally, as can be seen in FIG. 4A (insert), the encapsulated drop underwent negligible change in equilibrium shape with time, reaffirming the stability of the encapsulation layer.

Dependence of Extent of Encapsulation on the Volume of Interfacial Layer

Figure 4C:
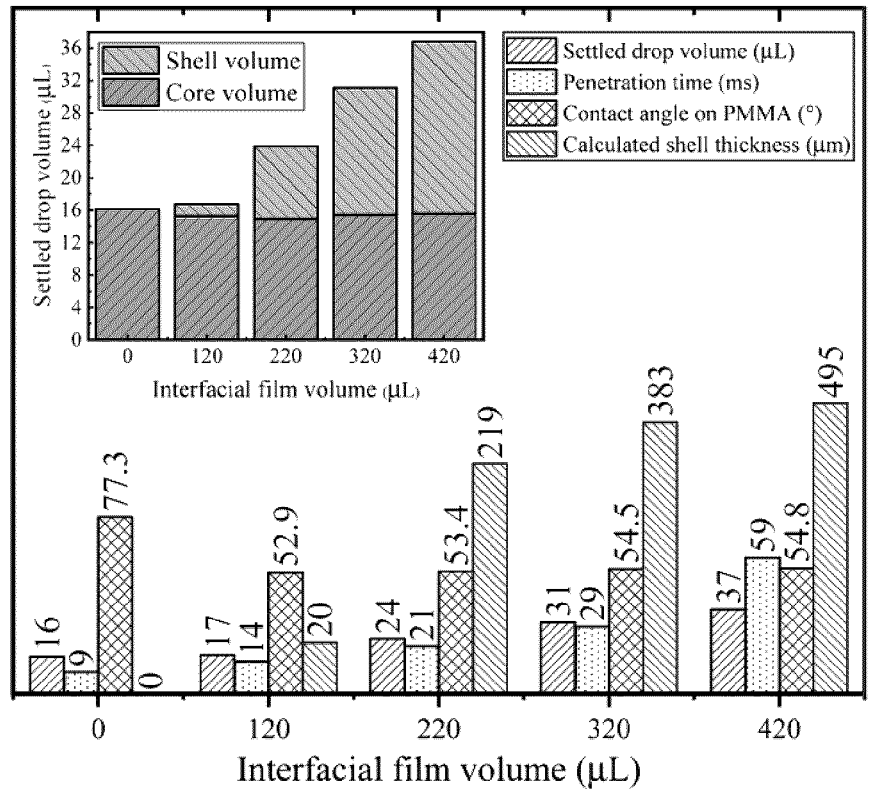

In the herein described method, the material properties of the interfacial layer and its volume (reflected in the equilibrium thickness of the resulting floating lens structure) are two key factors that dictate extent of encapsulation. Any increment in the interfacial layer thickness manifests in a corresponding enhancement in residence time of the core droplet inside the layer resulting in an augmented degree of interaction between the core drop and shell layer and a subsequent increase in the time required towards the completion of the encapsulation process. Consequently, upon penetration through the interfacial layer, the core droplet assimilates a higher volume of interfacial liquid with itself. This higher volume of encapsulating shell layer evincing itself in the form an increased post-encapsulation drop volume and estimated shell thickness as can be discerned from FIG. 4C. As expected, the core drop volume (the volume of the drop before it comes in contact with the interfacial layer) remained invariant with increase in interfacial film volume. Nevertheless, as shown in the inset of FIG. 4C any increase in interfacial film volume corresponded to a consistent increment in the shell volume. It was noted that as the encapsulation process was preceded by necking at the interface, a part of the core droplet got pinched off and trapped at the interfacial layer upon successful encapsulation, as also noted by Kumar et al. 3 Although the volume of the retained part of the core droplet was negligible in most of the cases, calculating the volume of encapsulating (shell) layer as the difference between the drop volumes before and after encapsulation gave a slight under-prediction in the extent of encapsulation.

For example, in FIG. 4C, the dependence on interfacial film thickness is explored by varying the value of $V_{film}$ in the range of 0-500 μL, while keeping the liquid combination fixed. The encapsulation experiments are carried out for five different values of $V_{film}$, namely, 0, 120, 220, 320 and 420 μL. For every value of $V_{film}$, the maximum thickness of the interfacial layer, $\delta_{max}$ was estimated using the method described in section S7 of Example 2, and was found to be 0, 2024, 2276, 2565 and 2845 μm respectively. The kinetic energy at impact was also kept constant by maintaining the same impact height H (7.5 cm in this case). Any increment in $\delta_{max}$ resulted in an enhancement in the viscous resistance which slowed the drop down by dissipating its momentum. As a result, the residence time of the core drop inside the interfacial layer increased. The increasing trend of residence time with increasing interfacial film thickness is captured in FIG. 4C in the form of penetration/encapsulation time, which is defined (even when there is no interfacial film) as the difference in time between two instances, namely, the first instance when the entire drop is inside the host liquid and the last instance when the drop is completely in air.

It was considered that there was a possibility of air entrapment when a droplet impacts on and enters a liquid pool. However, it is known that there exists a minimum threshold impact height below which there is practically no air entrapment. For the herein described experiments, particular attention was given to confirm this aspect, and from the high-speed photographs it was found that within the operating height (H) range of the study, air entrapment did not take place. Therefore, this volume enhancement was attributed to the volume gain of the core droplet during the process of its interfacial interaction with the intermediate liquid layer (consisting of liquid L2) and the subsequent formation of a liquid shell structure, if the volume of the aforementioned left-over portion of the core droplet is neglected. This stood as further evidence of successful encapsulation.

Figure 4D:
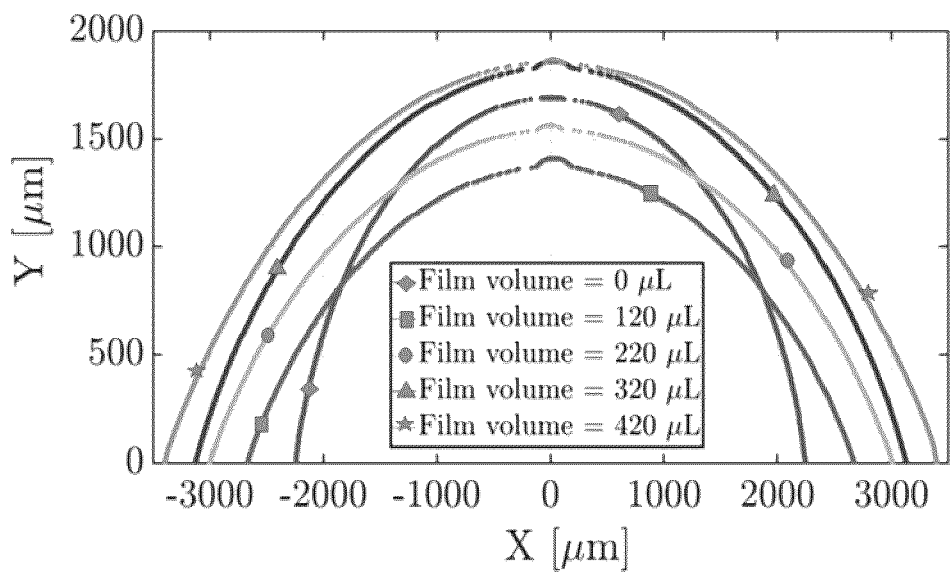

The contact angle being a thermodynamically intensive property (i.e., independent of the quantities involved) of the substrate-liquid combination, the dependence of observed contact angle on layer thickness is relatively insignificant. Even an interfacial canola film volume as low as 120 μL is found to be sufficient to give rise to an outer encapsulation layer that suppresses the intrinsic wetting signature of the core laser oil drop and exhibits conclusive resemblance with the wetting pattern of canola oil (the shell liquid), with a measured value of $\Theta=53.7°$. In FIG. 4D the extracted stable drop outlines on PMMA substrate have been illustrated to show the spreading of the drop upon encapsulation. It can be discerned from the inset plot that upon increasing the interfacial film volume, the contact line radius of the droplet increases to accommodate the additional shell volume. However, the contact angle remains invariant within the experimental error bar. This, in turn, endorses the applicability of alteration in wetting signature as a definitive evidence of a stable encapsulation.

Assessment of Practical Applicability: Protection from Aggressive Surrounding

Practical applicability of an encapsulation protocol depends extensively on its ability in safeguarding the core drop from an aggressive environment. To address this requirement, an experiment was designed where the core drop (L1) and host liquid medium (L3) are not internally compatible. For this purpose, ethylene glycol (density $p_1=1115$ kg/m$^3$, dynamic viscosity $\mu_1=16.9$ mPa-s and liquid-air surface tension $y_1=48$ mN/m) was chosen as the core liquid (L1) keeping other two liquids unaltered.

Due to its miscibility in water, ethylene glycol droplet could not retain its shape if it entered the host water bath directly (see FIG. 5A). However, when the same droplet was made to pass through an intermediate layer of canola oil (with $V_{film}=220$ μL) prior to entering the water bath, the drop attained an encapsulation layer of canola oil all around itself, which protected it from getting dissolved in the surrounding medium and consequently it retained itself even after settling down at the bottom of the water bath (see FIG. 5B). It is to be noted that in case of prolonged exposure to the surrounding water bath, the encapsulating layer tended to get detached from the core droplet owing to the thermodynamic preference of ethylene glycol getting dissolved in water. However, the timescale of the detachment process was much larger in comparison to the encapsulation timescale (with the drop remaining stable for ~150 s in comparison to the encapsulation timescale of ~50 ms in a typical experiment), which allows the user, for example, enough time to cure the encapsulated drop for further handling. Also, this delayed detachment of the encapsulating layer in aqueous medium can be a favorable attribute for pharmaceutical applications where the encapsulated drop can be hosted in another physiologically compatible medium (non-aqueous and immiscible with the core droplet). However when it comes into contact with the aqueous physiological medium upon being administered, it allows a delayed yet efficient release as the wrapping layer gets ultimately detached. Also, as highlighted earlier, a part of the core drop was retained back at the interface as the signature of successful penetration. In the post encapsulation top view of the interfacial layer illustrated in FIG. 5C, the existence of the left over portion of the impinging ethylene glycol drop inside the interfacial canola layer was noted. Existence of the encapsulating layer was also confirmed from the bottom view of the encapsulated drop captured under bright-field optical microscope (see FIG. 5D).

Generalizability of the Method for Higher Interfacial Film Volume

It was noted that the herein described method was not limited to formation of a lens-shaped interfacial layer. As mentioned earlier, for small volumes, the interfacial layer L2 attained a lens like shape with non-uniform thickness. However, upon increasing the volume, the lens shape disappeared, and the interfacial liquid formed a homogeneously distributed stratified layer instead. The herein described encapsulation technique remained applicable for this case as well.

Figure 6:
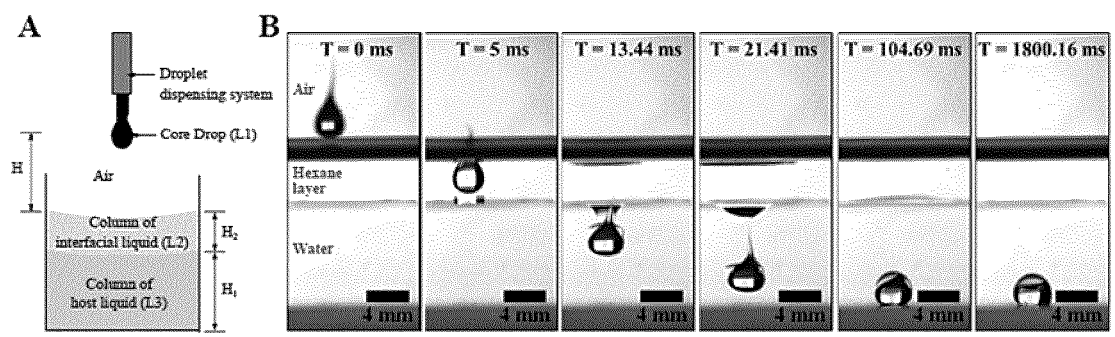
FIG. 6 depicts encapsulation with stratified intermediate liquid column instead of a thin interfacial film: (A) Schematic representation (not to scale) of the encapsulation process in presence of two stratified liquid columns, (B) A typical encapsulation experiment (represented in the form of a time series) demonstrating the journey of a core laser oil droplet through a stratified hexane layer (nominal height H$_2$=5 cm) stacked on top of a water bath (nominal height H$_1$=10 cm) for an impact height H=6 cm. The drop is seen to get encapsulated with hexane at the hexane-water interface. The wrapping layer can be distinctively noticed in the time stamps corresponding to T=104.69 ms and T=1800.16 ms.

A typical experiment highlighting this aspect is demonstrated in FIG. 6 where a cuvette was partially filled with 8.68 ml of water and then 4.34 ml of hexane (density $p_2=654.8$ kg/m 3, viscosity $\mu_2=0.297$ mPa-s, liquid-air surface tension $y_2=18.43$ mN/m) was dispensed on top of the water layer. The chosen volume combination resulted in a stratified layer of hexane with nominal height ($H_2$) of 5 cm stacked vertically on top of a water bath with nominal height ($H_1$) 10 cm for the chosen cuvette dimension. Afterwards, a laser oil drop was dispensed from a height (H) 6 cm above the hexane-air interface. The encapsulation process is illustrated in FIG. 6B in the form of a time series. As was expected from the trend of shell volume with interfacial film volume indicated in FIG. 4C, the volume of the shell liquid was significantly higher in comparison to the experiments presented earlier, owing to the increased volume of intermediate hexane layer. An accumulation of the shell liquid near the apex of the encapsulated drop was also observed. This was due to the significant density gradient between the core (laser oil) and the shell (hexane) liquids. Due to this accumulation, the encapsulating layer was no longer assumed uniform in thickness in this case.

Hexane was chosen as the shell liquid instead of canola oil because at an increased layer thickness of 5 cm, the intermediate layer of canola oil posed a significantly high viscous resistance in the penetration process of the core droplet. Consequently, the core droplet fails to separate from the interfacial layer if it does not have sufficient kinetic energy to overcome this viscous energy barrier. In the current embodiment of the experimental prototype, kinetic energy at the time of impact was directly proportional to the impact height. In the absence of any alternative external actuation (that aids increasing the kinetic energy of the drop), meeting this kinetic energy requirement mandated a prohibitively high impact height. Therefore, hexane, another liquid that is both lighter and immiscible in water and, at the same time, has much lower dynamic viscosity (0.297 mPa-s) compared to that of water (63.5 mPa-s), was chosen as an alternative shell liquid to demonstrate the concept.

CONCLUSION

Herein described is a liquid based encapsulation protocol which did not require the intricate fabrication/processing steps associated with thin elastic membranes, nanoparticles or colloidal assembly and yet was minimally restrictive regarding material properties, commercially scalable and relatively straightforward in execution. Apart from satisfying the fundamental requirements of efficiency and robustness, this encapsulation method exhibited promising prospects regarding its potential of encapsulating a wide range of surface active compounds (enzymes, nano-particles etc.). Successful encapsulation of the particulate suspension was an indirect indication of the same. This method may be used as a precursor to the existing encapsulation techniques where a multi-layered liquid drop with radially varying constitution can be obtained before the drop is enclosed by a polymer sheet or interfacial assembly of particles (viz. granular materials/colloidal surfactants etc.). Nevertheless this method finds its applicability as a standalone protocol as well where the constituents of the outermost shell layer may be manipulated to enable subsequent curing and hardened shell formation using established hardening techniques (e.g., ultraviolet treatment or coacervate formation). The wrapping process described herein may also be extended for multiple radial shell layers around a single core using a hybrid vertical stack consisting of several liquid columns.

Example 2—Supporting Information for Encapsulation with an Interfacial Liquid Layer: Robust and Efficient Liquid-Liquid Wrapping S1. Shape of the Interfacial Film Layer When the canola oil was dispensed dropwise on top of the water bath using a needle, the oil drops spread on top of the bath upon contact with water and ultimately attained a lens shape, where the bottom part of the lens was in contact with water while the top side faced air (see the schematic in FIG. 7A). However, from the experimental images (presented in FIG. 7B, 7C) it appeared that the oil lens was completely submerged in water and there was an intermediate water film that prevented any direct contact of the lens with air. It resembled a pseudo-total wetting state as outlined in the literature. Confirmation of the possibility of formation of any such intermediate water film was necessary as the existence of such a film of the surrounding medium would require the core drop to come in direct contact with the host liquid before it can interact with the interfacial wrapping layer, and any possible direct contact with the surrounding would violate one of the requirements of successful encapsulation, viz., the isolation of the core material from the surrounding. However for such a pseudo-total wetting state to form, the spreading parameter of the floating liquid (L2) on the bath (L3), $S_{23}$ should be negative with the spreading parameter of the bath (L3) on the floating liquid (L2), $S_{32}$ being positive. $S_{23}$ and $S_{32}$ are defined as, $$S_{23}=Y_3-y_2-Y_{23} \ \& \ S_{32}=Y_2-Y_3-Y_{23}$$

For the herein described experiments with canola oil (L2) layer on water (L3), $$S_{23}=(72-31.3-18.01)mN/m=22.6>0$$

$$S_{32}=(31.3-72-18.01)mN/m=-58.71mN/m<0$$

Therefore, as both the theoretical requirements are unmet, existence of such a pseudo-total wetting state was considered theoretically infeasible.

It was noted that this was an imaging artefact arising due to the curved concave meniscus shape of water in glass cuvette. To reaffirm this, a simple experiment was conducted. After a canola film layer (with film volume of 220 µL) was formed on top of the water bath, a water droplet was dispensed on top of the film with a pipette. Had there been an intermediate water film on top of the canola layer, the dispensed water droplet would have spread instantaneously due to direct contact between two similar liquid surfaces. However, the droplet did not spread and was seen to retain itself. This served as a practical confirmation that there was no intermediate water film between the canola lens and water.

S2. Measurement of Surface and Interfacial Tensions

Whenever possible surface and interfacial tension values were calculated in-house using pendant drop tensiometry. A slightly modified version of the open source framework OpenDrop v1.1 developed earlier by Berry et al. (7) was used to analyze the axis-symmetric drop shapes to determine the surface (or interfacial) tension values. The experimental value for surface tension for the base case of pure (undyed) canola was benchmarked against the values available in literature (31 mN/m) to ensure accuracy of the used tensiometry setup.

Every value of surface (interfacial) tension thus determined was an average of five different measurements and were reported alongside an error bar in terms of standard deviation of 5 observations. Due to very low interfacial energy of canola oil—laser oil combination, it did not tend to form a proper pendant drop shape, instead it formed a vertical column of canola oil terminated by a spherical interface. Interfacial tension in this case was estimated using a method based on the balance between hydrostatic and Laplace pressure. For a second opinion, this combination of liquids was tested by Future Digital Scientific Corp, NY, USA with the commercially available OCA20 Data Physics optical contact angle device (Data Physics Instruments, Germany) and their reported value (2.22 mN/m) was found to be in close agreement with the one measured in-house.

Surface tension measurements were also carried out after a suspension was prepared by thoroughly mixing canola oil with the yellow partially oil-soluble dye. As can be seen in Table 1, the surface tension of canola oil remained invariant upon addition of dye.

S3. Estimation of Volume and Thickness of Encapsulation Layer Using Image Processing First the outlines of the drops were extracted from the grey-scale experimental images (the 2D projection of the drops) employing a Sobel-Feldman edge detector algorithm before discretizing the obtained drop shapes to a pixel level precision. The volume, cross-sectional area and surface area of the drops were calculated thereafter assuming axial symmetry of the drops around a central vertical axis. A theoretical framework to estimate the encapsulated film thickness was also developed utilizing the extracted outline of the encapsulated drop under the assumption that the film was of uniform thickness.

Figure 8:
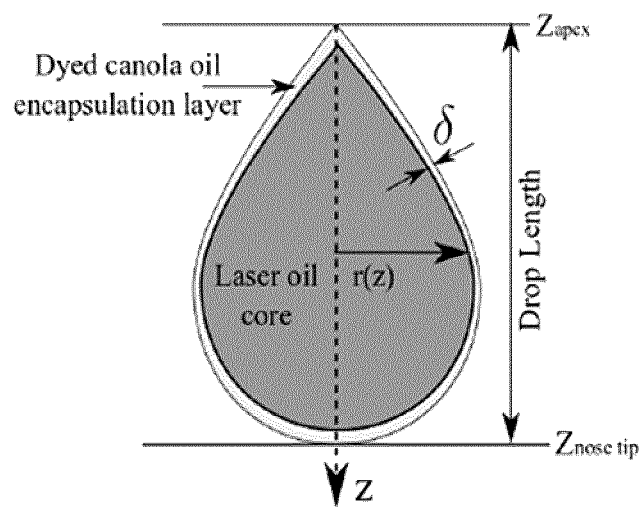
FIG. 8 depicts a schematic representation (not to scale) of the 2-D projection of an axis-symmetric encapsulated drop with uniform shell thickness.

Once the outline of the drop was determined using the edge detector algorithm, the local radius of the drop, r was expressed as a function of z. Thereafter the volume of both the core drop as well as the encapsulated drop were estimated by approximating the drops to be a vertical stack of multiple cylindrical sections with radius r(z) and height 1 pixel. FIG. 8 provides a schematic representation of the axis-symmetric encapsulated drop shape that was used to calculate the geometric properties of the drops.

$$V_{core} = \int_{z_{apex}}^{z_{nose\ tip}} \pi\{r(z)\}^2 dz \quad \text{Eq. (S1)}$$

$$V_{core+shell} = \int_{z_{apex}}^{z_{nose\ tip}} \pi\{r(z)+\delta\}^2 dz$$

$$\therefore V_{shell} = \int_{z_{apex}}^{z_{nose\ tip}} \pi\{\delta^2 + 2r(z)\delta\}dz = \pi\delta^2 L_{drop} + \pi\delta A_{cs,core}$$

Here $V_{core}$ is the volume of the core, $V_{shell}$ is the volume of the shell layer, $\delta$ is the thickness (uniform) of the shell layer, $L_{drop}$ is the vertical span of the drop expressed as $L_{drop}=z_{nose\ tip}-z_{apex}$ and $A_{cs,\ core}$ is the cross-sectional area of the core drop about a central vertical axis. It was considered that the resulting shape of the stable encapsulated droplet on glass substrate can justifiably be assumed to be spherical and axis-symmetric (as can be seen in the final timestamps of FIG. 1B, 1C and FIG. 3A, FIG. 5B), which significantly simplified the process for ballpark estimation of encapsulation thickness. In that case film thickness, $\delta$ can be estimated as $$\delta = \left(\sqrt[3]{\frac{3V_{core+shell}}{4\pi}} - \sqrt[3]{\frac{3V_{core}}{4\pi}}\right).$$

S4. Equilibrium Thermodynamic Analysis for Success and Stability of Encapsulation From thermodynamic perspective, the transition of the core drop in air at a height H above the interface to an encapsulated drop is spontaneous only when the change in Gibbs potential is negative in the process (see FIG. 9A).

$$\Delta G = G_{after} - G_{before} < 0$$

A simplified theoretical estimate for the stability of the encapsulated drops was used under the following assumptions:

The droplets (both encapsulated and unencapsulated) are spherical in shape.
The shell layer has an all-around uniform thickness.
Layer thickness $\delta$ is much less when compared to the core drop radius Rc i.e. $\delta \ll Rc$
The change in surface area of the interfacial oil layer before and after encapsulation is negligible. Therefore, the change in interfacial energy of this layer due to the encapsulation process needs not to be accounted for.

Assuming both the unencapsulated and encapsulated drops to be spherical in shape was a reasonable approximation. For a given enclosed volume, a spherical shape has the lowest surface area and consequently, the lowest surface energy, making it the thermodynamically most stable shape among all possible configurations. Therefore, it can be inferred that the criterion governing successful encapsulation for the most stable initial configuration is a conservative one and automatically holds true for the actual pendant drop shape that has a higher surface area. For the encapsulated drops, the drops were considered after the post encapsulation interfacial disturbances had subsided. The drops then were seen to attain near-spherical shape.

The fourth approximation was justified with experimental observation that the volume of the detached (shell forming) layer accounted to no more than 10% of the total interfacial film volume. So, if a spherical shape was assumed for a ballpark estimate, then the change in surface area comes to be <6.67%, which can justifiably be neglected. With these approximations, the change in Gibbs potential between the states represented in FIG. 9A (a) and FIG. 9A (b) were calculated as:

$$\Delta G = G_{after} - G_{before} = A_{12}\gamma_{12} + A_{23}\gamma_{23} - A_1\gamma_1 - m_d g H =$$
$$4\pi R_c^2 \gamma_{12} + 4\pi(R_c+\delta)^2 \gamma_{23} - 4\pi R_c^2 \gamma_1 - \frac{4}{3}\pi R_c^3 \rho_1 g H \quad \text{Eq. (S2)}$$

where $R_c$ is the radius of core droplet, $\delta$ is the thickness of the encapsulating layer, $m_d$ is the mass of the core droplet, H is the impact height, g is the acceleration due to gravity, $y_{ij}$ is the interfacial tension between phase i and j and $A_{ij}$ is the surface area between phase i and j, where $(i,j) \in \{1,2,3\}$ and $y_i$ is the surface tension (with air) of phase i.

$$\text{As } \delta \ll R_c; 4\pi(R_c+\delta)^2 \approx 4\pi R_c^2 \quad \text{Eq. (S3)}$$

$$\therefore \Delta G \approx 4\pi R_c^2 (\gamma_{12} + \gamma_{23} - \gamma_1) - \frac{4}{3}\pi R_c^3 \rho_1 g H$$

For $\Delta G < 0$;

$$H > \frac{3(\gamma_{12} + \gamma_{23} - \gamma_1)}{\rho_1 g R_c} \quad \text{Eq. (S4)}$$

Eq. (S4) is the necessary condition for the formation of an encapsulated drop from a purely equilibrium thermodynamic perspective. However, H being a positive quantity, if $(y_{12}+y_{23}-y_1)$ is negative then Eq. (S4) gets automatically satisfied, making $(y_{12}+y_{23}-y_1)<0$ a sufficient condition for encapsulation.

For the herein described experiments with water (L3), canola oil (L2) and laser oil (L1), $(y_{12}+y_{23}-y_1) = (2.22+18.01-50) mN/m = -29.77 mN/m < 0$ Therefore, theoretical formation of an encapsulation layer is thermodynamically favorable at all impact heights for the abovementioned liquid combination and therefore the impact height H should not pose any restrictions on the success of the process. However as outlined in FIG. 3C, impact height (manifested in impact Weber number) played an important role in successful encapsulation. This is because the thermodynamic estimate only considers the free energy differences between the two equilibrium states. And G being a state variable, the change in Gibbs potential does not reflect anything about process that lead to the transformation. The key underlying assumption here was that the path leading to encapsulation is reversible and therefore there is no loss of energy in the process. However, in practice the process is highly irreversible with the viscous dissipation during the drop's journey through the interfacial layer being the primary source of irreversibility that remains unaccounted for.

Therefore, it was considered that $y_{12}+y_{23}<y_1$ may not be a completely sufficient condition. There remains a possibility that the drop would not get encapsulated even after the above condition was satisfied. It is because the drop needs to possess sufficient kinetic energy ($\approx$the potential energy of the core drop immediately before its detachment from the dispensing needle tip, $m_d g H$, neglecting viscous dissipation during its traversal through air) not only to overcome the energy barrier posed by the interfacial energy difference between the two states but also to compensate for the viscous dissipation while breaking through the interfacial layer. If it does not have enough kinetic energy then even after having an energetically favorable interfacial tension combination, the droplet will not be able to separate from the interfacial layer and instead will get trapped in there. The experiment presented in FIG. 3B and all the points highlighted in circles in FIG. 3C correspond to this scenario.

If the energy loss due to viscous dissipation is $\Delta E_{visc}$, then the effective criteria becomes $$m_d g H > \Delta E_{visc} + \Delta G \quad \text{Eq. (S5)}$$

$$\therefore \frac{4}{3}\pi R_c^3 \rho_1 g H > \Delta E_{visc} + 4\pi R_c^2 (\gamma_{12}+\gamma_{23}-\gamma_1)$$

$\Delta E_{visc}$ is the result of a complex dynamic interaction between the core droplet, the interfacial layer and the host liquid bath.

S4.2 Theoretical Criterion for Stability of Encapsulation

Attaining an encapsulation structure does not assure its stability as the wrapping layer (L2) might get detached from the core leaving the core droplet (L2) exposed to the surrounding liquid (L3), if this transition is energetically favorable. Therefore, for the encapsulated drop to be stable, the free energy change between encapsulated state and the unwrapped state (where the core drop is exposed to the same surrounding liquid bath after detachment of the shell layer) should be positive (see FIG. 9B for a schematic representation of the two aforementioned states). The free energy change between the two states can be expressed as, $$\Delta G = G_{unencaps,L3} G_{endcaps,L3} = A_1 Y_{13} - A_{12} Y_{12} -$$
$$A_{23} Y_{23} = 4\pi R_c^2 y_{13} - 4\pi R_c^2 y_{12} - 4\pi(R_c+\delta)^2 y_{23} \approx 4$$
$$\pi R_c^2 (Y_{13} - Y_{12} - Y_{23}) \quad \text{Eq. (S6)}$$

Here $G_{encaps,L3}$ is the Gibbs potential of the encapsulated drop in the surrounding bath of L3 (FIG. 9B (a)), while $G_{unencaps,L3}$ corresponds to the Gibbs potential of the state after the wrapping layer is detached and the core drop is exposed to L3 (FIG. 9B (b)). It was assumed that the post detachment surface area of the wrapping layer (L2) is negligible and therefore can be neglected in the calculation of free energy change. This was considered a justifiable assumption given the fact that the thickness of the shell layer is much less than the diameter of the core drop ($\delta << Rc$). From Eq. (S5), for $\Delta G > 0$ $(Y_{13}-Y_{12}-Y_{23}) > 0$ ∴ $Y_{13} > Y_{12} + Y_{23}$                        Eq. (S7)

For the herein described experiments with water (L3), canola oil (L2) and laser oil (L1), $(y_{13}-Y_{12}-y_{23})(39.4-2.22-18.01) mN/m = 19.17 mN/m > 0$ Therefore, it was considered that the resulting encapsulated drops were thermodynamically stable.

S5. Fluorescent characterization of the encapsulation layer

To reaffirm the existence of a stable encapsulation layer around the core droplet, fluorescent signatures of the participating entities were analyzed. Canola oil (L2, interfacial liquid) has no background fluorescent properties. Therefore, it was mixed with a fluorescent oil soluble dye (see Example 1) to facilitate visualization. Upon being exposed to 365 nm ultraviolet excitation (in air), the laser oil drop showed a visible bluish emission. However, the emission wavelength of the dyed canola oil droplet fell in the yellow range of the visible spectrum, as can be seen in FIG. 10A.

For comparison, the fluorescent images of the encapsulated and the unencapsulated were also captured under the same excitation wavelength of 365 nm. As can be seen in FIG. 10B, the unencapsulated core drop (laser oil) mimicked the bluish fluorescent signature of the bare laser oil drop while the encapsulated drop (laser oil drop wrapped in a layer of canola oil) exhibited a yellowish emission spectrum similar to that of the dyed canola oil drop. This indirectly affirmed the existence of an outer wrapping layer of canola oil.

S6. Non-Existence of Water Film (~Nm) Between Substrate and Underwater Droplets

The possibility of formation of a very thin intermediate layer of the surrounding medium while studying underliquid wetting interaction between a substrate-liquid combination was been hypothesized. To attribute the change in wetting behavior as evidence to successful encapsulation, it was important to theoretically check any such possibility of an intermediate layer formation and confirm that the alteration in wetting behavior was not due to such an intermediate water film. For this purpose, first the underwater contact angle of both laser oil and canola oil drops were calculated without considering any thin film. Thereafter, formation of a sandwiched thin water layer (see FIG. 11) was assumed and the theoretical contact angle was calculated accordingly using a modified version of the Young's equation as reported in (6). The calculated values are tabulated in Table 2.

It can be concluded from Table 2 that the experimental observations were in close agreement with the theoretical predictions when not assuming a thin film. However, an assumption of a thin water layer rendered the theoretical estimates to deviate significantly from the experimental outcomes. Therefore, it was concluded that no such thin film forms between the PMMA substrate and the drops (both encapsulated and unencapsulated). Hence, the alteration in wetting signature could be attributed to successful all-around encapsulation.

S7. Estimation of Maximum Thickness of the Interfacial Oil Layer

The interfacial layer had a maximum film thickness, $\delta_{max}$ at the centre of the lens. Although, in the experiments $V_{film}$ was the parameter that could be precisely controlled, it was desirable to map the output quantities (resulting shell thickness, encapsulated volume etc.) with respect to $\delta_{max}$ instead of $V_{film}$. This was because $\delta_{max}$ is a more fundamental representation of the effect (e.g., the imposed viscous resistance) of the interfacial layer on the process dynamics. However, due to the concave shape of the water meniscus, the complete profile of the bi-convex floating lens could not be captured. The downward curved meniscus obscured the side view of the top portion (air-side) of the lens. However, the shape of the water side could be captured. To reconstruct the entire profile, the lens was assumed to be an intersection of two spheres of different radii along a common circular plane, the diameter of which was equal to the diameter of the contact line. Thereafter, with some geometric calculations, the profile of the air side was reconstructed using the known value of $V_{film}$ and measured shape of the bottom part of lens. This allowed the estimation of $\delta_{max}$ for different values of $V_{film}$.

The shape of the interfacial liquid (L2) layer is dependent on the values of surface and interfacial tensions and the volume of the dispensed liquid. Upon being dispensed on the water (L3)—air interface, the canola oil (L2) film took the shape of a bi-convex lens with one side in contact with water while the other side is exposed to air.

Figure 12:
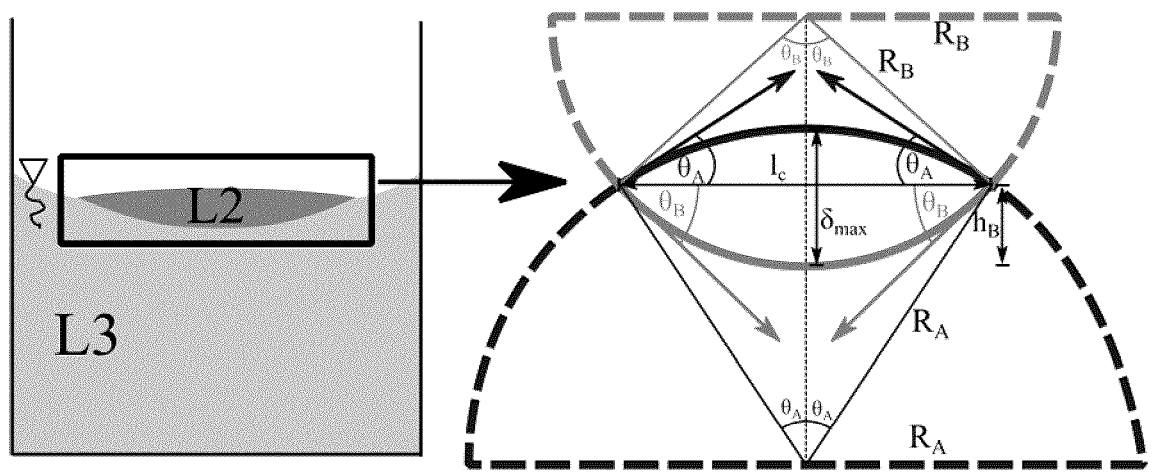
FIG. 12 depicts a cross-sectional view of the geometric profile of the interfacial oil layer—Representation of a liquid lens as an intersection of two spheres with different radii at a common circular plane.

The lens can be approximated to be the intersection of two spheres of different radii at a common circular plane, the diameter of which is equal to the diameter of the contact line ($l_c$). The top portion (air side) and bottom portion (water side) of the lens therefore can be represented geometrically by caps of two spheres with radii R A and R B respectively. And the two aforementioned spherical caps subtend angles 2θA and 2θB at their respective center, where θ A and θ B are the air and water side contact angles of the liquid lens. See FIG. 12 for a schematic representation of the cross-sectional view of such a lens with relevant geometric parameters. $\delta_{max}$ is the maximum thickness of the entire lens and h B is the maximum thickness of the spherical cap on the water side (bottom).

$l_c = 2R_A \sin \theta_A = 2R_B \sin \theta_B$

Due to the concave shape of water-air meniscus, experimental visualization of the entire lens shape becomes difficult as the downward curved meniscus obscures the side view of the top part of the lens. However, as can be seen in FIG. 7C, the water side (bottom portion) of the lens can be imaged from the side-view. The diameter of the contact line $l_c$ and the maximum thickness on the water side h B can therefore be unambiguously determined from the image. Due to spherical geometry, $\theta_B$ can be obtained thereafter from $l_c$ and $h_B$ as, $$\theta_B = 2\tan^{-1}\left(\frac{2h_B}{l_c}\right).$$

Now the total volume of the lens $V_{film}$ (combining the individual volumes of the two spherical caps) can be expressed as a function of $l_c$, $\theta_A$, and $\theta_B$ as $$V_{film}(l_C, \theta_A, \theta_B) = \qquad \text{Eq. (S8)}$$

$$\frac{\pi l_c^3}{24}\left(2\csc\theta_A^3 + \cot\theta_A^3 - 3\cot\theta_A\csc\theta_A^2 + 2\csc\theta_B^3 + \cot\theta_B^3 - 3\cot\theta_B\csc\theta_B^2\right)$$

The volume of the dispensed liquid is known. Also, $I_c$ and $\theta_B$ are determined from the experimental image. Eq. S8 can be solved now to obtain the value of $\theta_A$ which allows us to reconstruct the entire shape of the interfacial oil lens.

The maximum thickness of the lens, $\delta_{max}$ can be determined thereafter from $$\delta_{max} = \frac{l_c}{2}\left(\tan\frac{\theta_A}{2} + \tan\frac{\theta_B}{2}\right) \qquad \text{Eq. (S9)}$$

A general observation is that both the diameter of contact line, $I_c$ and maximum film thickness $\delta_{max}$ increase with increase in the volume of interfacial layer. The calculated values of $I_c$ and $\delta_{max}$ are tabulated in Table 3 for different values of interfacial film volume, $V_{film}$ used in this work.

Figure 13:
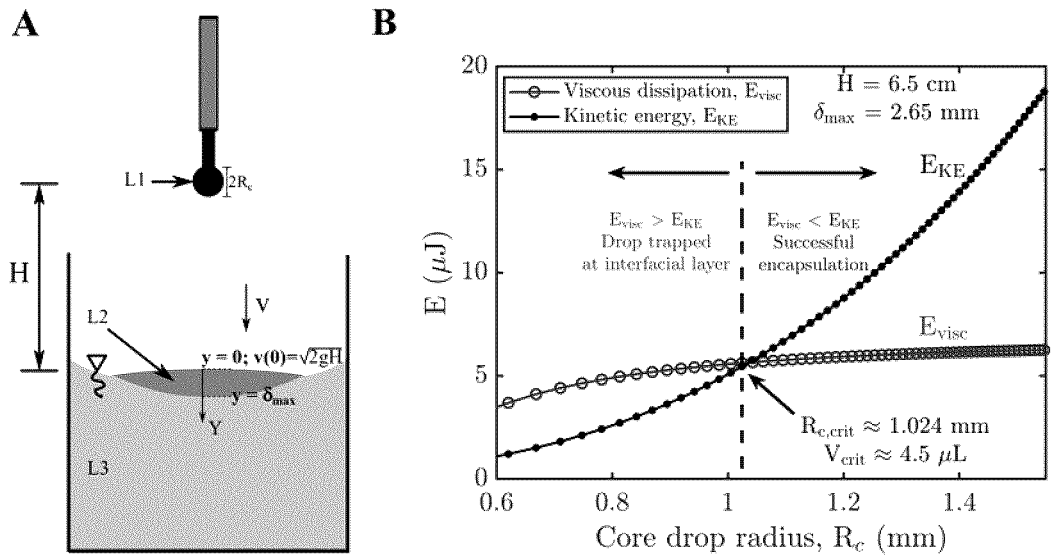
FIG. 13 depicts a theoretical estimation of viscous dissipation during a drop's downward motion through an interfacial layer: (A) Schematic (not to scale) representation of the simplified framework for estimation of viscous dissipation. (B) Theoretical dependence of the viscous dissipation and the impact kinetic energy on the radius of the core drop. Here H=6.5 cm and δ$_{max}$=2.65 mm. Minimum drop volume (theoretical) for successful encapsulation is found to be 4.5 μL.

S8. Theoretical Estimation of Viscous Dissipation During the Drop's Traversal Through Interfacial Layer Evaluation of energy loss due to viscous resistance is needed to get an estimate of the minimum allowable drop size for successful encapsulation. However, complete theoretical estimation of the same is particularly challenging due to the involvement of three continuously evolving liquid interfaces. A simplified theoretical estimate was obtained by assuming the drop's motion through the interfacial layer to be equivalent to the motion of a non-deformable spherical drop through a viscous medium of thickness $\delta_{max}$. The Stokes' drag on the drop and the resulting energy dissipation were calculated and compared against the impact kinetic energy (see below). It was observed that with a decrease in drop size both viscous dissipation, $E_{visc}$ and kinetic energy, $E_{KE}$ reduces but $E_{KE}$ reduces at a faster rate and below a critical drop radius, $R_{c,coit}$ the value of viscous dissipation becomes higher than the impact kinetic energy. This critical radius denotes the theoretical threshold for minimum drop size that can be successfully encapsulated for a given impact height H and maximum interfacial layer thickness $\delta_{max}$. As an example, a core drop with volume as small as 4.5 µL can be successfully encapsulated with a layer of L2 for an impact height of 6.5 cm and interfacial film volume of 370 µL (see FIG. 13).

During its downward motion through the interfacial layer (L2) the drop experiences a viscous drag which slows it down. If the kinetic energy of the impinging droplet is not sufficient to overcome this viscous barrier, the drop gets trapped at the interfacial layer and cannot get encapsulated despite having a thermodynamically favorable tendency of encapsulation by L2 (i.e., $\Delta G_{formation} < 0$).

Complete theoretical estimation of this viscous drag is particularly challenging because of the involvement of three continually deforming fluid interfaces. However, demonstrated herein is a simplified analytical approach to provide a ballpark estimate of the viscous dissipation. A schematic representation (not to scale) of the simplified system is presented in FIG. 13A. The droplet's motion was approximated by assuming as if a spherical non-deformable drop is moving through a viscous layer of thickness $\delta_{max}$ and during its traversal it experiences Stokes' drag. Therefore, the simplified governing equation can be written as:

$$m_d \frac{dv}{dt} = mg - F_B - F_{visc}$$

$$\Rightarrow \frac{4}{3}\pi R_c^3 \rho_1 \frac{dv}{dt} = \frac{4}{3}\pi R_c^3(\rho_1 - \rho_2)g - 6\pi\mu_2 R_c v$$

$$\Rightarrow \frac{4}{3}\pi R_c^3 \rho_1 v \frac{dv}{dy} = \frac{4}{3}\pi R_c^3(\rho_1 - \rho_2)g - 6\pi\mu_2 R_c v$$

$$\Rightarrow v\frac{dv}{dy} + \frac{9\mu_2}{2R_c^2 \rho_1}v = \left(1 - \frac{\rho_2}{\rho_1}\right)g;$$

where $c_1 = \frac{9\mu_2}{2R_c^2 \rho_1}$ and $c_2 = \left(1 - \frac{\rho_2}{\rho_1}\right)g.$ $$\therefore v\frac{dv}{dy} + c_1 v = c_2$$

Rearranging and integrating with respect to y $$\int \frac{v\,dv}{c_2 - c_1 v} = \int dy + k$$

where k is a constant of integration $$\Rightarrow -\frac{1}{c_1}\int\left[\frac{c_2}{c_1(c_1 v - c_2)} + \frac{1}{c_1}\right]dv = \int dy + k$$

$$\therefore -\frac{c_2}{c_1^2}\ln(c_1 v - c_2) - \frac{v}{c_1} = y + k$$

After some algebraic simplification Eq can be expressed in the following form $$\left(\frac{c_1 v - c_2}{c_2}\right)\exp\left(\frac{c_1 v - c_2}{c_2}\right) = \frac{1}{c_2}\exp\left(-\frac{(y+k)c_1^2}{c_2} - 1\right).$$

This is a transcendental equation which can be expressed in terms of Lambert W function (product logarithm function) as follows, $$\left(\frac{c_1 v - c_2}{c_2}\right) = W\left[\frac{1}{c_2}\exp\left(-\frac{(y+k)c_1^2}{c_2} - 1\right)\right] \qquad \text{Eq. (S10)}$$

$$\therefore v(y) = \frac{c_2}{c_1}\left(W\left[\frac{1}{c_2}\exp\left(-\frac{(y+k)c_1^2}{c_2} - 1\right)\right] + 1\right).$$

The integration constant k can be determined from the following boundary condition at y=0, $$v(0) = \sqrt{2gH},$$

where H is the vertical separation between the needle tip and the interfacial layer.

The value of k is obtained by imposing the aforementioned boundary condition and solving Eq. (S10) using the symbolic toolbox in MATLAB. The velocity profile of the droplet, v is obtained thereafter as a function of the downward traversal coordinate y. Now the energy loss, $E_{visc}$ during the core droplet's traversal through the interfacial layer can be obtained by integrating the viscous drag, $F_{visc}$ over the traversal path.

$$\therefore E_{visc} = \int_0^{\delta_{max}} F_{visc} dy = \int_0^{\delta_{max}} 6\pi\mu_2 R_c v(y) dy. \quad \text{Eq. (S11)}$$

Also, the impact kinetic energy of the core droplet, EKE can be expressed as, $$E_{KE} = m_d g H = \frac{4}{3}\pi R_c^3 \rho_1 g H.$$

When $\Delta G_{formation} < 0$, a competition between viscous dissipation, $E_{visc}$ and kinetic energy, $E_{KE}$ dictates the success of encapsulation.

As the drop volume is reduced (and consequently, the drop radius) both $E_{visc}$ and $E_{KE}$ reduces but $E_{KE}$ reduces at a faster rate and below a critical drop radius, $R_{c,crit}$ the viscous dissipation becomes higher than the impact kinetic energy. This critical radius denotes the theoretical threshold for minimum drop size that can be successfully encapsulated for a given impact height H and maximum interfacial layer thickness $\delta_{max}$. A typical trend of $E_{visc}$ and $E_{KE}$ vs Rc is presented in FIG. 13B for H=6.5 cm and $\delta_{max}$=2.65 mm (with a corresponding $V_{film}$=370 µL). According to the theoretical prediction, a drop with volume as small as 4.5 µL, which corresponds to a drop radius of 1.024 mm, can be successfully encapsulated with a layer of L2.

For further experimental details, results, and discussion, please see Misra, S.; Trinavee, K., Gunda, N. S. K., Mitra, S. K. Encapsulation with an interfacial liquid layer: Robust and efficient liquid-liquid wrapping. Journal of Colloid and Interface Science 558 (2020) 334-344, the entire content of which, including the supporting information, is hereby incorporated by reference.

REFERENCE LIST (1) Abkarian, M.; Proti_ere, S.; Aristoff, J. M.; Stone, H. A. Gravity-induced encapsulation of liquids by destabilization of granular rafts. Nat. Commun. 2013, 4, 1895.
(2) Jambon-Puillet, E.; Josserand, C.; Protiere, S. Drops floating on granular rafts: a tool for liquid transport and delivery. Langmuir 2018, 34, 4437-4444.
(3) Kumar, D.; Paulsen, J. D.; Russell, T. P.; Menon, N. Wrapping with a splash: Highspeed encapsulation with ultrathin sheets. Science 2018, 359, 775-778.
(4) Loscertales, I. G.; Barrero, A.; Guerrero, I.; Cortijo, R.; Marquez, M.; Ganan-Calvo, A. Micro/nano encapsulation via electrified coaxial liquid jets. Science 2002, 295, 1695 1698.
(5) Utada, A.; Lorenceau, E.; Link, D.; Kaplan, P.; Stone, H.; Weitz, D. Monodisperse double emulsions generated from a microcapillary device. Science 2005, 308, 537-541.
(6) Trinavee, K.; Gunda, N. S. K.; Mitra, S. K. Anomalous Wetting of Underliquid Systems: Oil Drops in Water and Water Drops in Oil. Langmuir 2018, 34, 11695-11705.
(7) Berry, J. D.; Neeson, M. J.; Dagastine, R. R.; Chan, D. Y.; Tabor, R. F. Measurement of surface and interfacial tension using pendant drop tensiometry. J. Colloid Interface Sci. 2015, 226-237.
(8) Misra, S.; Trinavee, K., Gunda, N. S. K., Mitra, S. K. Encapsulation with an interfacial liquid layer: Robust and efficient liquid-liquid wrapping. Journal of Colloid and Interface Science 558 (2020) 334-344.

TABLE 1

Variation of surface tension with addition of partially oil soluble particle-based dye.

| Dye amount | No dye | 0.35 gm/100 ml | 1.05 gm/100 ml | 2.5 gm/100 ml |
|---|---|---|---|---|
| Surface tension (mN/m) | 33.3 ± 1.5 | 35.87 ± 1 | 34.63 ± 2 | 32.36 ± 1.5 |

TABLE 2

Confirmation of non-existence of an intermediate water film. The first column represents the theoretically estimated contact angle for the concerned case using under-liquid Young's equation without considering any intermediate thin film while the second column provides a theoretical estimate of contact angle assuming a thin water film between the substrate and the oil droplet using a modified formulation of Young's equation (as proposed in (6)). The last column reports the experimentally observed values of contact angle for the respective cases.

| Test cases | Theoretical contact angle-without thin film (°) | Theoretical contact angle-with thin film consideration (°) | Experimental contact angle (°) |
|---|---|---|---|
| Canola (drop) in water | 45.33 | 105.24 | 52.89 |
| Laser oil (drop) in water | 70.17 | 131 | 77 |

TABLE 3

Dependence of contact line diameter and maximum layer thickness on interfacial film volume

| Film volume, $V_{film}$ (µL) | Contact line diameter, $I_c$ (mm) | Maximum thickness of interfacial layer, $\delta_{max}$ (mm) |
|---|---|---|
| 30 | 8.15 | 1.14 |
| 80 | 10.82 | 1.73 |
| 100 | 12.06 | 1.74 |
| 120 | 12.22 | 2.02 |
| 160 | 14.14 | 2.02 |
| 220 | 15.60 | 2.28 |
| 270 | 17.09 | 2.33 |
| 320 | 17.72 | 2.56 |
| 370 | 18.72 | 2.65 |
| 420 | 19.26 | 2.84 |
| 470 | 19.88 | 2.99 |
| 500 | 20.17 | 3.08 |
| 550 | 20.67 | 3.23 |
| 600 | 21.21 | 3.34 |
| 650 | 21.71 | 3.45 |
| 850 | 22.72 | 4.13 |
| 900 | 23.31 | 4.15 |
| 1150 | 25.85 | 4.31 |
| 1200 | 26.31 | 4.34 |
| 1400 | 27.45 | 4.65 |

The embodiments described herein are intended to be examples only. Alterations, modifications and variations can be effected to the particular embodiments by those of skill in the art. The scope of the claims should not be limited by the particular embodiments set forth herein, but should be construed in a manner consistent with the specification as a whole.

All publications, patents and patent applications mentioned in this Specification are indicative of the level of skill those skilled in the art to which this invention pertains and are herein incorporated by reference to the same extent as if each individual publication patent, or patent application was specifically and individually indicated to be incorporated by reference.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

What is claimed is:

1. A method of forming an encapsulated core material, the method comprising:
    providing an interfacial fluid and providing a host fluid, the interfacial fluid being layered on the host fluid;
    dispensing a core material from a distance above the interfacial fluid layer; and
    passing the dispensed core material through the interfacial fluid and into the host fluid such that the interfacial fluid forms a shell around the core material,
    thereby forming the encapsulated core material.

2. The method of claim 1, wherein providing the interfacial fluid layered on the host fluid comprises:
    providing a volume V of the interfacial fluid selected to provide the interfacial fluid layered on the host fluid; or
    dispensing the interfacial fluid on top of the host fluid.

3. The method of claim 2, wherein the shell has a thickness T and modifying the volume V adjusts the thickness T.

4. The method of claim 1, further comprising:
    forming the core material, wherein the core material is a core droplet;
    providing the core material, wherein the core material is a core solid.

5. The method of claim 4, wherein forming the core droplet comprises dispensing the fluid from a syringe pump and needle assembly.

6. The method of claim 1, wherein dispensing the core material comprises:
    dropping the core material from a height H from the interfacial fluid; and/or imparting a first kinetic energy to the core material, expressed in impact Weber number $We_i$.

7. The method of claim 6, wherein:

$$H > \frac{3(\gamma_{12} + \gamma_{23} - \gamma_1)}{\rho_1 g R_e},$$

where g is gravitational acceleration, Rc is radius of the core material assuming spherical geometry, $p_1$ is density of the core material, $\gamma_{12}$ is core material/interfacial fluid interfacial tension, $\gamma_{23}$ is interfacial fluid/host fluid interfacial tension, and $\gamma_1$ is air/core material interfacial tension; and/or $$We_i = \frac{\rho_1 v^2 l_c}{\gamma_1} \approx \frac{2\rho_1 g H l_c}{\gamma_1}$$

where v is velocity of the core material immediately before impacting the interfacial fluid, g is acceleration due to gravity, $p_1$ is density of the core material, and $l_c$ is characteristic length scale typically expressed as radius of the core material assuming spherical shape, H is impact height, and $\gamma_1$ is air/core material interfacial tension.

8. The method of claim 1, wherein dispensing the core material comprises:
    actuating the core material from a distance D from the interfacial fluid; and/or
    imparting a second kinetic energy to the core material.

9. The method of claim 8, wherein actuating comprises accelerating the core material using pressure, jetting, electrostatic interactions, electrohydrodynamic actuation, or a centripetal force.

10. The method of claim 1, wherein
    when passing the dispensed core material, the only fluid the core material contacts is the interfacial fluid; and/or
    wherein forming the encapsulated core material comprises protecting the core material with the shell, preventing the core material from contacting the host fluid.

11. The method of claim 1, wherein forming the encapsulated core material further comprises:
    hardening the core material or the shell; and/or
    curing the core material to form a hardened core material or curing the shell to form a hardened shell.

12. The method of claim 11, wherein curing the shell comprises:
    exposing the core material or the shell to ultraviolet radiation;
    triggering a coacervate formation; or
    exposing the shell to heat.

13. The method of claim 1, further comprising enclosing the encapsulated core material.

14. A method of forming a multi-layered encapsulated core material comprising a core material and a shell, the method comprising:
    providing an interfacial fluid layer and a host fluid, the interfacial fluid layer comprising at least a first and a second interfacial fluid, the first interfacial fluid being layered on the second interfacial fluid and the second interfacial fluid being layered on the host fluid;
    dispensing a core material from a distance above the interfacial fluid layer; and
    passing the dispensed core material through the interfacial fluid layer and into the host fluid such that the interfacial fluid layer forms a shell around the core material, the shell comprising the at least first and second interfacial fluid,
    thereby forming the multi-layered encapsulated core material.

15. An encapsulated core material composition, comprising:
    a host fluid; and
    an encapsulated core material in the host fluid,
    the encapsulated core material comprising a core material and an interfacial fluid, the interfacial fluid encapsulating the core material with a shell.

16. The composition of claim 15, wherein the core material has a density $p_1$, the interfacial fluid has a density $p_2$, the host fluid has a density $p_3$, and wherein:

$$p_2 < p_3 < p_1; \text{ or}$$

$$p_1 > p_2 > p_3.$$

17. The composition of claim 15, wherein, for the encapsulated core material in the host fluid, $$Y_{13} > Y_{12} + Y_{22}$$

where $\gamma_{13}$ is core material/host fluid interfacial tension, $\gamma_{12}$ is core material/interfacial fluid interfacial tension, and $\gamma_{23}$ is interfacial fluid/host fluid interfacial tension.

18. The composition of claim 15, wherein the shell protects the core material from the host fluid and/or prevents the core material from contacting the host fluid.

19. The composition of claim 15, wherein:
the core material and the host fluid are incompatible;
the core material is miscible with the host fluid; and/or
the core material is reactive with the host fluid.

20. The composition of claim 15, wherein the core material, the interfacial fluid, or the host fluid comprise an additive.

21. The composition of claim 20, wherein the additive is a pharmaceutical compound, an enzyme, a microparticle, a nanoparticle, a surfactant, a mineral, a nutrient, an oil, a fish oil, a probiotic, a polymer, a water-treatment compound, or a soil-treatment compound.

22. The composition of claim 15, wherein:
the core material is a solid or a fluid;
the interfacial fluid is a liquid, a liquid mixture, an oil, a solution, a suspension, a liquid polymer, a liquid polymer mixture, a liquid agar gel, a liquid gelatin, or a liquid cellulose; and/or
the host fluid is a liquid, a liquid mixture, a solution, a suspension, a liquid polymer, a liquid polymer mixture, a liquid agar gel, a liquid gelatin, or a liquid cellulose.

23. The composition of claim 22, wherein when the core material is:
a solid, the solid is a polymer, a nut, or a seed; or
a fluid, the fluid is a liquid, a liquid mixture, a solution, a suspension, a liquid polymer, a laser liquid, or a liquid polymer mixture.

24. The composition of claim 15, wherein the shell is a hardened shell.

25. The composition of claim 24, wherein the hardened shell comprises a crosslinked interfacial fluid or a coacervate formation formed from the interfacial fluid.

26. The composition of claim 15, further comprising an enveloping layer enclosing the encapsulated core material.

27. The composition of claim 26, wherein the enveloping layer comprises a polymer sheet or an interfacial assembly of particles.

28. The composition claim 15, wherein the shell comprises at least a first and a second interfacial fluid, and the core material is encapsulated with a first shell formed from the first interfacial fluid, and the first shell is encapsulated with a second shell formed from the second interfacial fluid.

29. The method of claim 1, further comprising delivering the encapsulated core material:
to a subject, the encapsulated core material comprising a pharmaceutical compound;
to a subject for delayed release of a pharmaceutical compound, the encapsulated core material comprising the pharmaceutical compound;
to a subject in a cosmetic product;
to a subject for delayed release of an additive from a cosmetic product, the encapsulated core material comprising the additive;
in an emulsion;
in a food product; or
for encapsulating a food product.

30. The method of claim 6, wherein dropping the core material comprises dispensing the core material from a syringe pump and needle assembly.

* * * * *

UNITED STATES PATENT AND TRADEMARK OFFICE
CERTIFICATE OF CORRECTION

| | | |
|---|---|---|
| PATENT NO. | : 12,145,120 B2 | Page 1 of 1 |
| APPLICATION NO. | : 17/432848 | |
| DATED | : November 19, 2024 | |
| INVENTOR(S) | : Sushanta Mitra et al. | |

It is certified that error appears in the above-identified patent and that said Letters Patent is hereby corrected as shown below:

In the Claims

At Claim 17, Column 44, Line 61: please replace "$\gamma_{22}$" with -- $\gamma_{23}$ --

At Claim 28, Column 46, Line 9: please replace "The composition claim 15" with -- The composition of claim 15 --

Signed and Sealed this
First Day of July, 2025

Coke Morgan Stewart
*Acting Director of the United States Patent and Trademark Office*